(12) United States Patent  
Harris

(10) Patent No.: US 9,233,206 B2
(45) Date of Patent: Jan. 12, 2016

(54) CONTINUOUS FEED HYPODERMIC SYRINGE WITH SELF CONTAINED CARTRIDGE DISPENSER

(75) Inventor: Arthur Harris, New York, NY (US)

(73) Assignee: Arthur Harris, New York, NY (US)

( * ) Notice: Subject to any disclaimer, the term of this patent is extended or adjusted under 35 U.S.C. 154(b) by 1881 days.

(21) Appl. No.: 11/847,791

(22) Filed: Aug. 30, 2007

(65) Prior Publication Data
US 2008/0058732 A1    Mar. 6, 2008

Related U.S. Application Data

(60) Provisional application No. 60/823,974, filed on Aug. 30, 2006, provisional application No. 60/862,283, filed on Oct. 20, 2006.

(51) Int. Cl.
*A61M 5/28* (2006.01)
*A61M 5/24* (2006.01)
(Continued)

(52) U.S. Cl.
CPC . *A61M 5/28* (2013.01); *A61M 5/20* (2013.01); *A61M 5/24* (2013.01); *A61M 5/2425* (2013.01); *A61M 5/001* (2013.01); *A61M 5/31511* (2013.01); *A61M 5/3202* (2013.01); *A61M 5/326* (2013.01); *A61M 2005/005* (2013.01); *A61M 2005/206* (2013.01); *A61M 2005/3118* (2013.01); *A61M 2005/3121* (2013.01); *A61M 2005/3152* (2013.01)

(58) Field of Classification Search
CPC ... A61M 5/288; A61M 5/1626; A61M 5/162; A61M 5/283; A61M 5/282; A61M 5/28; A61M 5/24

USPC .......... 604/110, 192–199, 232, 233, 237, 263
See application file for complete search history.

(56) References Cited

U.S. PATENT DOCUMENTS 2,526,365 A * 10/1950 Jorgensen ............... A61M 5/24
                                                       604/229
2,888,924 A *  6/1959 Dunmire ............... A61M 5/282
                                                       604/196

(Continued)

FOREIGN PATENT DOCUMENTS

CH           404870      12/1965
EP           0154593      9/1985
(Continued)

*Primary Examiner* — Aarti B Berdichevsky
*Assistant Examiner* — Matthew A Engel
(74) *Attorney, Agent, or Firm* — Jack Schwartz and Associates, PLLC

(57) ABSTRACT

A hypodermic syringe and a plurality of single use cartridges able to be successively loaded into said syringe for providing rapid dispensing of a medicant to numerous users without contamination. The cartridges are continuously fed through the syringe to inoculate patients quickly and efficiently. An operator inserts a needle into a patient by pushing a trigger. Prior to insertion, a disinfectant is dispersed from the cartridge to maintain sterility. An operator then pushes in a plunger forcing the medication through the needle into the patient. The needle is pulled back with the plunger out of the patient's skin and back into the cartridge. A new cartridge on a clip is then advanced into the syringe to inoculate the next patient. The syringe and cartridge dispenser further maintains a sterile environment during successive vaccinations reducing the transmission of any disease from patient to patient.

3 Claims, 28 Drawing Sheets

(51) Int. Cl.
*A61M 5/20* (2006.01)
*A61M 5/00* (2006.01)
*A61M 5/315* (2006.01)
*A61M 5/32* (2006.01)
*A61M 5/31* (2006.01)

(56) References Cited

U.S. PATENT DOCUMENTS

| | | | | |
|---|---|---|---|---|
| 3,084,688 A * | 4/1963 | McConnaughey | A61M 5/24 | 604/232 |
| 3,134,380 A * | 5/1964 | Armao | A61M 5/001 | 604/198 |
| 3,136,313 A * | 6/1964 | Enstrom | A61M 5/2033 | 604/139 |
| 3,496,937 A * | 2/1970 | Balson | A61M 5/20 | 604/132 |
| 3,512,524 A * | 5/1970 | Drewe | A61M 3/00 | 206/365 |
| 3,557,787 A * | 1/1971 | Cohen | A61M 5/31596 | 604/90 |
| 3,678,931 A * | 7/1972 | Cohen | A61M 5/284 | 604/201 |
| 3,793,770 A * | 2/1974 | Johnson | A01M 17/00 | 231/7 |
| 3,797,490 A * | 3/1974 | Hurschman | A61M 5/28 | 604/196 |
| 3,810,469 A * | 5/1974 | Hurschman | A61M 5/284 | 206/222 |
| 3,820,542 A * | 6/1974 | Hurschman | A61M 5/28 | 604/196 |
| 3,965,897 A * | 6/1976 | Lundquist | A61M 5/1408 | 604/246 |
| 3,967,621 A * | 7/1976 | Schwarz | A61M 5/288 | 604/192 |
| 3,980,083 A * | 9/1976 | Elliott | A61J 1/2089 | 604/203 |
| 4,303,069 A * | 12/1981 | Cohen | A61M 5/288 | 604/192 |
| 4,388,011 A * | 6/1983 | Smith | A46B 11/0027 | 132/308 |
| 4,424,057 A * | 1/1984 | House | A61M 5/31596 | 604/88 |
| 4,639,250 A * | 1/1987 | Rycroft | A61M 5/282 | 604/201 |
| 4,725,267 A * | 2/1988 | Vaillancourt | A61M 5/3202 | 604/192 |
| 4,795,432 A * | 1/1989 | Karczmer | A61M 5/3257 | 604/110 |
| 4,822,340 A * | 4/1989 | Kamstra | A61M 5/2066 | 604/135 |
| 4,983,164 A * | 1/1991 | Hook | A61M 5/2066 | 604/139 |
| 5,019,048 A * | 5/1991 | Margolin | A61M 5/282 | 604/153 |
| 5,080,648 A * | 1/1992 | D'Antonio | A61M 5/2425 | 604/135 |
| 5,163,908 A * | 11/1992 | Lambert | A61M 5/326 | 604/110 |
| 5,176,655 A * | 1/1993 | McCormick | A61M 5/3275 | 604/192 |
| 5,190,521 A * | 3/1993 | Hubbard | A61M 5/422 | 604/117 |
| 5,295,963 A * | 3/1994 | Deeks | A61M 5/3257 | 604/110 |
| 5,295,972 A * | 3/1994 | Mischenko | A61M 5/3275 | 604/192 |
| 5,308,322 A * | 5/1994 | Tennican | A61M 5/1408 | 604/183 |
| 5,318,522 A * | 6/1994 | D'Antonio | A61M 5/2425 | 604/135 |
| 5,419,771 A * | 5/1995 | Kriesel | A61M 5/1409 | 128/DIG. 12 |
| 5,894,015 A * | 4/1999 | Rechtin | | 422/301 |
| 6,056,716 A * | 5/2000 | D'Antonio | A61M 5/24 | 604/134 |
| 6,086,562 A * | 7/2000 | Jacobsen | A61M 5/20 | 604/131 |
| 6,132,395 A * | 10/2000 | Landau | A61M 5/30 | 604/236 |
| 6,261,264 B1 * | 7/2001 | Tamaro | A61M 5/3271 | 128/919 |
| 6,302,868 B1 * | 10/2001 | Mohammad | A61B 5/1438 | 604/192 |
| 6,394,992 B1 * | 5/2002 | Sjoholm | A61M 5/162 | 141/313 |
| 6,398,762 B1 * | 6/2002 | Vetter | A61M 5/002 | 604/171 |
| 6,733,465 B1 * | 5/2004 | Smutney | A61B 5/1438 | 600/576 |
| 6,860,871 B2 * | 3/2005 | Kuracina | A61B 5/1411 | 604/192 |
| 6,932,795 B2 * | 8/2005 | Lopez | A61M 39/045 | 251/142 |
| 7,354,422 B2 * | 4/2008 | Riesenberger | A61M 5/3273 | 604/198 |
| 7,361,163 B2 * | 4/2008 | Cohen | A61M 5/20 | 206/366 |
| 7,604,613 B2 * | 10/2009 | Crawford | A61M 5/3234 | 604/110 |
| 7,637,891 B2 * | 12/2009 | Wall | A61K 9/0019 | 604/131 |
| 7,669,597 B2 * | 3/2010 | Sullivan | A61M 15/0028 | 128/200.14 |
| 7,976,477 B2 * | 7/2011 | Roe et al. | A61B 5/1411 | 600/583 |
| 7,985,216 B2 * | 7/2011 | Daily | A61J 1/2096 | 604/131 |
| 7,988,664 B2 * | 8/2011 | Fiser | A61M 25/0618 | 604/110 |
| 8,187,224 B2 * | 5/2012 | Wyrick | A61M 5/2033 | 604/117 |
| 8,308,691 B2 * | 11/2012 | Woehr | A61B 5/1411 | 604/164.08 |
| 8,529,522 B2 * | 9/2013 | Cohen | A61M 5/20 | 206/366 |
| 8,574,214 B2 * | 11/2013 | Kuhn | A61M 5/288 | 604/411 |
| 8,945,070 B2 * | 2/2015 | Holmes | A61M 5/24 | 604/232 |
| 2002/0147431 A1 * | 10/2002 | Lopez | A61M 39/045 | 604/256 |
| 2004/0116847 A1 * | 6/2004 | Wall | A61K 9/0019 | 604/93.01 |
| 2006/0129122 A1 * | 6/2006 | Wyrick | A61M 5/2033 | 604/506 |
| 2006/0173408 A1 * | 8/2006 | Wyrick | A61M 5/2033 | 604/110 |
| 2008/0319385 A1 * | 12/2008 | Kriesel | A61M 5/14244 | 604/88 |
| 2010/0310782 A1 * | 12/2010 | Wawrzyniak | A61B 17/00491 | 427/445 |
| 2013/0218089 A1 * | 8/2013 | Davies | A61M 5/3294 | 604/191 |

FOREIGN PATENT DOCUMENTS

| | | |
|---|---|---|
| GB | 2319184 | 5/1998 |
| TR | 200400990 | 1/2006 |
| WO | WO 03/037410 | 5/2003 |

* cited by examiner

CONTINUOUS FEED HYPODERMIC SYRINGE WITH SELF CONTAINED CARTRIDGE DISPENSER

CROSS-REFERENCE TO RELATED APPLICATIONS

This application claims the benefit of U.S. Provisional Application No. 60/862,283 filed Oct. 20, 2006 and U.S. Provisional Application No. 60/823,974 filed Aug. 30, 2006, which are herein incorporated by reference.

FIELD OF THE INVENTION

The present invention relates to hypodermic syringes and, more specifically, to a continuous feed hypodermic syringe with a self contained cartridge dispenser.

BACKGROUND OF THE INVENTION

Presently, medical caregivers may dispense liquids or vaccines to patients via hypodermic syringes. After each dosage is administered, the medical caregiver must re-load a different syringe with a new dosage for administration to the next patient. However, it is believed that these methods are inefficient when a large population must be inoculated in a short amount of time.

One patent disclosing a pre-filled syringe and syringe tip assembly is U.S. Pat. No. 5,624,405 issued to Futagawa et al. Futagawa et al. disclose a pre-filled syringe, a sealing member, and a tip member. However, a noted drawback associated with Futagawa et al. is that the there is no continuous feed. A new pre-filled syringe must be prepared for each patient, which takes time and is inefficient.

Another patent disclosing a cartridge for an injection device is U.S. Pat. No. 5,709,662 issued to Olive et al. Olive et al. describe an assembly for automatically injecting a fluid into the body. Similar to Futagawa et al., the Olive et al. assembly requires preparation of a new syringe for each patient, which takes time and is inefficient.

While these devices may be suitable for the purposes for which they were designed, they would not be suitable for the purposes of the present invention, as hereinafter described.

SUMMARY OF THE INVENTION

An apparatus and method for continuously feeding and injecting a liquid and/or vaccine including an injection device able to receive a plurality of individual single use cartridges and/or containers each of which include a hypodermic syringe. The injection device operates to dispense a liquid or vaccine from the individual single use cartridge retained in a single use cartridge or container.

It is an object to provide a continuous feed hypodermic syringe with a self contained cartridge dispenser.

Another object is to provide a single use cartridge which prevents cross-contamination.

Still another object is to provide a hypodermic syringe for use in the field of hospitals and clinics.

Another object is to provide a hypodermic syringe that may operate manually and is simple to use in a variety of conditions such as lesser developed areas having few amenities typically associated with medical treatment.

Yet another object is to provide a hypodermic syringe preferably made from an inert, transparent plastic so as to observe and easily correct any malfunction associated with the syringe and or the injection mechanism that may occur.

The continuous feed hypodermic syringe is an apparatus and method for injecting medications into a large number of recipient patients that may be used in both clinical settings such as hospital and non-clinical field settings where conditions for treating patients may be primitive. Additionally, the term patient as used herein may include a human or non-human that is in need of medical treatment using a medicament that is delivered via injection.

The apparatus is formed from a pre-loaded medicament cartridge that includes a needle or a sharp and a spring positioned around the needle. The medicament cartridge is sealed and sterilized. The cartridge consists of a hollow tube which contains the liquid or vaccine in a collapsible and sterile container. The hollow tube may be transparent and made from an inert plastic. The hollow tube or cartridge is sealed after it is filled. A hollow needle is attached to the container and includes a plastic accordion core surrounding the needle. The front end of the tube is sealed by a thin membrane and the back end of the tube is sealed by a cap so that the entire contents remain sterile. The cap may include a membrane. The cartridge is designed such that the needle injected into the patient to deliver the medication is prevented from contacting the user by the spring surrounding the needle. The spring is compressed and reveals the needle immediately prior to injection and, upon removal from the patient, expands and re-covers the needle. The pre-loaded cartridge has a predetermined medicinal dosage enabling a user to treat a large number of patients for the same disease or ailment without having to prepare a dosage amount for each patient. Additionally, the pre-loaded cartridge is designed to reduce at least one of injuries that may be caused by the needle, possibility of contaminating the needle and/or medicine, accidental injections and/or dispensing of medication.

Additionally, the cartridges may be snapped or formed onto a clip or alternatively, to a flexible belt. When the male and female protrusions on the cartridge and clip mate, the cartridge is secured to the clip and prevented from being set on the clip in the wrong direction. The clip may be in the form of a belt with a plurality of cartridges positioned on the belt and extending along the length of the clip.

The clip is inserted into the barrel near the mouth of the barrel from either side. The clip is positioned so that when inserted, protrusions in the barrel are received by matching indentations in the clip as the clip is pulled through the barrel. When the cartridge has been used, the operator pulls the clip further through the barrel to remove the spent cartridge and move an adjacent cartridge into position within the barrel. The adjacent cartridge is correctly positioned when the spring loaded protrusions in the barrel are able to extend through the indentations or recesses in the clip surrounding the cartridge adjacent to the preceding spent cartridge.

The hypodermic syringe dispenser may have a pistol-shape. However, this is for purposes of example only, and the dispenser may take other shapes. The dispenser may have a pistol grip for ease in handling during operation. The dispenser may further include a barrel to hold the cartridge used for injecting the vaccine, replacing the spent cartridge, and advancing a new cartridge into position.

The barrel acts as the guide for a piston ensuring direct contact with the cartridge when activated. The piston is used to engage the cartridge and insert a needle into a patient therefrom. The barrel may include a hollow section running the length of the barrel, through which a piston is pushed and returns. When the piston is forced forward, a spring connected thereto is uncoiled and a plunger and pressure plate is moved forward with the piston. The plunger is then further pushed in by an operator, which causes medicine in the cartridge to be dispensed into the patient through the needle. The rear end of the piston is fastened to a compression spring. Upon release of the pressure on the piston, the spring pulls the piston back into position for a new injection and at the same time, returning the trigger to its initial position.

The piston includes sprockets or gears on a base thereof which are engaged by matching sprockets or gears on the trigger. When the trigger is squeezed and thereby pivoted, the sprockets on the piston and trigger engage one another and cause the piston to advance towards the cartridge. The base of the trigger includes a notched end for ease of moving the trigger back into its rest position should the trigger be stuck. The piston is returned to the original position when the trigger recoils.

The front end of the piston is hollowed out to form a depression of substantially 1 inch or more in depth. The depth of the depression is described for purposes of example only and the depth is dependent on the length of the vaccine container. This depth of substantially 1 inch leaves a thin wall surrounding the hollowed section which is substantially $1/8^{th}$ of an inch thick. The leading edge of the wall is slightly tapered and sharpened so that it cuts through the rear membrane and slips more easily around the medication container. However, this is for purposes of example only and any known depression sizes, wall sizes and wall shapes may be used as long as they are able to perform the intended objective.

When the trigger is released, the piston moves back, propelled by the recoil force of the spring connected to the rear of the piston.

In an alternate embodiment, the cartridges are linked together on a flexible belt. The flexible belt may include a plurality of sprocket holes between the cartridges on the belt. The sprocket holes may be used to advance the belt after each injection, thereby placing a new, unused cartridge in position for the next injection. The flexible belt may be rolled up and inserted into a drum. The drum may be insulated and chilled if necessary thereby allowing the dispenser to dispense a plurality of different types of medications that may require different storage conditions.

The rear or base of the cartridge tube has a raised lip or rim similar to that on a bullet. The raised lip serves to guide the cartridge into position into a slot into the dispensing mechanism. The leading edges or corners of the top and bottom rims are rounded to aid the entrance of the rim into the slots of the syringe and prevent catching when inserted into the slot. The rim withstands the impact and pressure from the spring driven piston. Therefore, the shape of the rim is designed so as to provide the maximum resistance to the impact of the piston by providing a maximum lip when positioned in the slot. The raised lip further retains the cartridge tube in the dispenser and on the clip. The raised lip may also prevent the cartridge tube from being ejected from the dispenser when the piston pressure is applied to a rear edge of the cartridge.

The barrel includes a slot along one side and a spring powered piston. The spring powered piston, when activated, penetrates the rear of the cartridge tube through the rear membrane. The piston exerts a force on the tube and causes the accordion folds of the core to be collapsed thereby ejecting the needle through the membrane. A disinfectant is dispersed prior to the injection in order to maintain a sterile environment. Upon ejection, the needle penetrates the layers of skin of the patient. Then, an operator pushes in a plunger attached to the pressure plate and extending out of the back of the syringe unit. The plunger collapses the contents of a medicine container and injects medicine into the patient through the needle or sharp. When the medication is fully injected into the patient, the operator pulls back the plunger into its original location and the needle/sharp goes back into the cartridge. A spring activated lever attached to a gear is selectively activated to advance the clip/belt containing the unused cartridges.

The barrel acts as the guide for the piston ensuring direct contact with the cartridge when activated. The piston is activated by a spring attached to a rear end thereof. Alternatively, the spring is actuated by a trigger mechanism positioned under the barrel as is commonly known in the art of firearms. The piston includes a notch proximate the rear end. A trigger assembly engages the notch to hold the piston in position when the piston is drawn back by a hinged, extended lever. The hinge permits the lever to be moved close to the barrel to make a smaller parcel for shipment. Alternatively, the lever may be rigidly attached to the piston. The lever is fastened to the piston at a right angle to the barrel. The slot along the side of the barrel permits the lever to extend out on one side of the barrel when the lever is pulled back and guides the piston during this action.

When the piston is released, the piston moves forward, propelled by the force of the released spring at the rear of the piston. When the outer front lip of the wall of the piston reaches the cartridge tube, the front lip penetrates the membrane and the continuing forward motion of the piston surrounds the container of liquid. However, the container does not as yet receive any pressure so as to cause it to dispense any liquid. The spring pressure continues to force the piston forward. Now, the leading edge of the piston reaches and presses against the base of the hollow core. This pressure forces the core outward. When the pointed end of the core reaches the membrane, it presses against and tears through the membrane.

The piston continues to move forward and the base of the hollowed out part of the piston reaches the rear end of the container with the liquid. The disinfectant is dispersed and the needle is forced out of the membrane and penetrates the patient's skin. The plunger is pushed by an operator onto the base of the liquid container which collapses the container, forcing the liquid into and through the hollow needle. The liquid is now forced out through the needle and into the patient. After the container is empty of its liquid, the operator pulls the plunger back into its original position and the needle is withdrawn from the patient. The core surrounding the needle re-expands.

Additionally, when the plunger is pulled back, the belt, having a tooth of a gear engaging a sprocket hole in the belt, advances the belt. The gear makes enough of a turn so as to advance the belt one notch, replacing a new cartridge for the used one. Because the amount of dosage may vary, the piston will have plugs supplied to fill some of the space in the hollow core of the piston, if needed.

BRIEF DESCRIPTION OF THE DRAWING FIGURES

In order that the invention may be more fully understood, it will now be described, by way of example, with reference to the accompanying drawing in which.

DETAILED DESCRIPTION OF THE INVENTION

Figure 1:
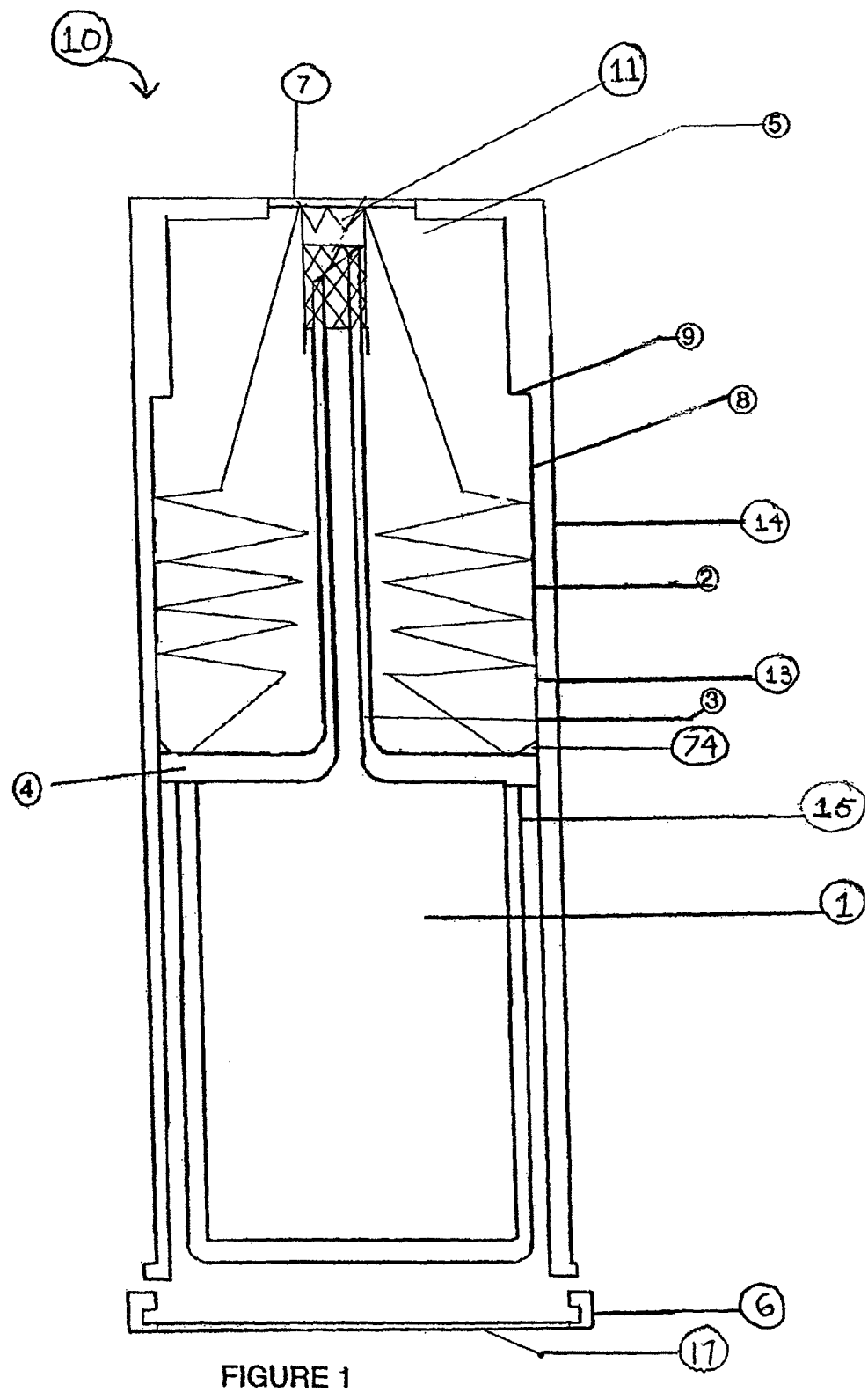
FIG. 1 is a side view of a cartridge for use with continuous feed hypodermic syringe according to invention principles.

The following discussion describes in detail the invention. This discussion should not be construed, however, as limiting the invention to that particular embodiment. Practitioners skilled in the art will recognize numerous other embodiments as well.

Turning now to the drawings, in which similar reference characters denote similar elements throughout the several views, FIGS. 1 through 12 illustrate a continuous feed hypodermic syringe with self contained cartridge dispenser which is indicated generally by the reference numeral 10. FIGS. 13 through 19 illustrate a continuous feed hypodermic syringe with self contained cartridge dispenser according to an additional embodiment of the present claimed invention. FIGS. 20 through 25 illustrate a continuous feed hypodermic syringe with self contained cartridge dispenser according to an additional embodiment of the present claimed invention. FIGS. 26 through 29 illustrate a continuous feed hypodermic syringe with self contained cartridge dispenser according to alternate embodiment of the present claimed invention.

FIG. 1 is a side view of a cartridge for use with continuous feed hypodermic syringe according to invention principles. Rear cap 6 includes a single membrane 17. A space 5 is positioned between membrane 7 and a needle. The space 5 stores a small amount of disinfectant sterilizing fluid which, when the membrane is ruptured, is released thereby sterilizing the area on the patient to be injected as well as the needle passing therethrough. The space 5 may be a reservoir containing alcohol as a disinfectant, for example.

The cartridge for use with the continuous feed syringe is a sealed, flexible housing that includes a container 1 having a prepared, proper dose of the medication to be injected using the device. The container is sealed at one end with a needle 3 extending therefrom. The needle 3 differs from a standard needle in that it has a wide, flared, trumpet shaped base 4 that reaches the inner walls 13 of the cartridge surrounding it. The flexibility of the container 1 enables compression thereof by a force which causes evacuation of the medication from within the container 1 through the needle 3. The device for injecting the medication will be described hereinafter with respect to FIG. 2. The container 1 has a circumference smaller than the inner cartridge wall so as to allow sufficient space for a tube to surround the container 1 when the compression force acts on the tube causing the tube to move in a direction opposite the direction of the compression force. The wide collar or base 4 of the needle 3 enables the tube edge to make contact and transfer the compression force to the needle 3 causing the needle to move in a direction towards the front membrane 7.

A spring 2 having a central channel extending vertically therethrough is positioned within the inner walls of the cartridge and surrounds the needle 3 such that the needle 3 extends through the central channel. The spring 2 includes a cutting tip 11 that is notched and is able to pierce the forward membrane 7 of the cartridge. The notched tip 11 spreads the membrane 7 apart when it is pierced and the needle extends out from the cartridge and into the patient. Medication contained within the container 1 is injected into the patient, through the needle 3, in a manner that will be described with respect to FIG. 2 below.

A stop 9, a shoulder 8, an outer wall 14 of the cartridge, a tit 74 which prevents the needle 3 from prematurely extending and a space for the piston wall 15 are additionally shown in FIG. 1.

Figure 2:
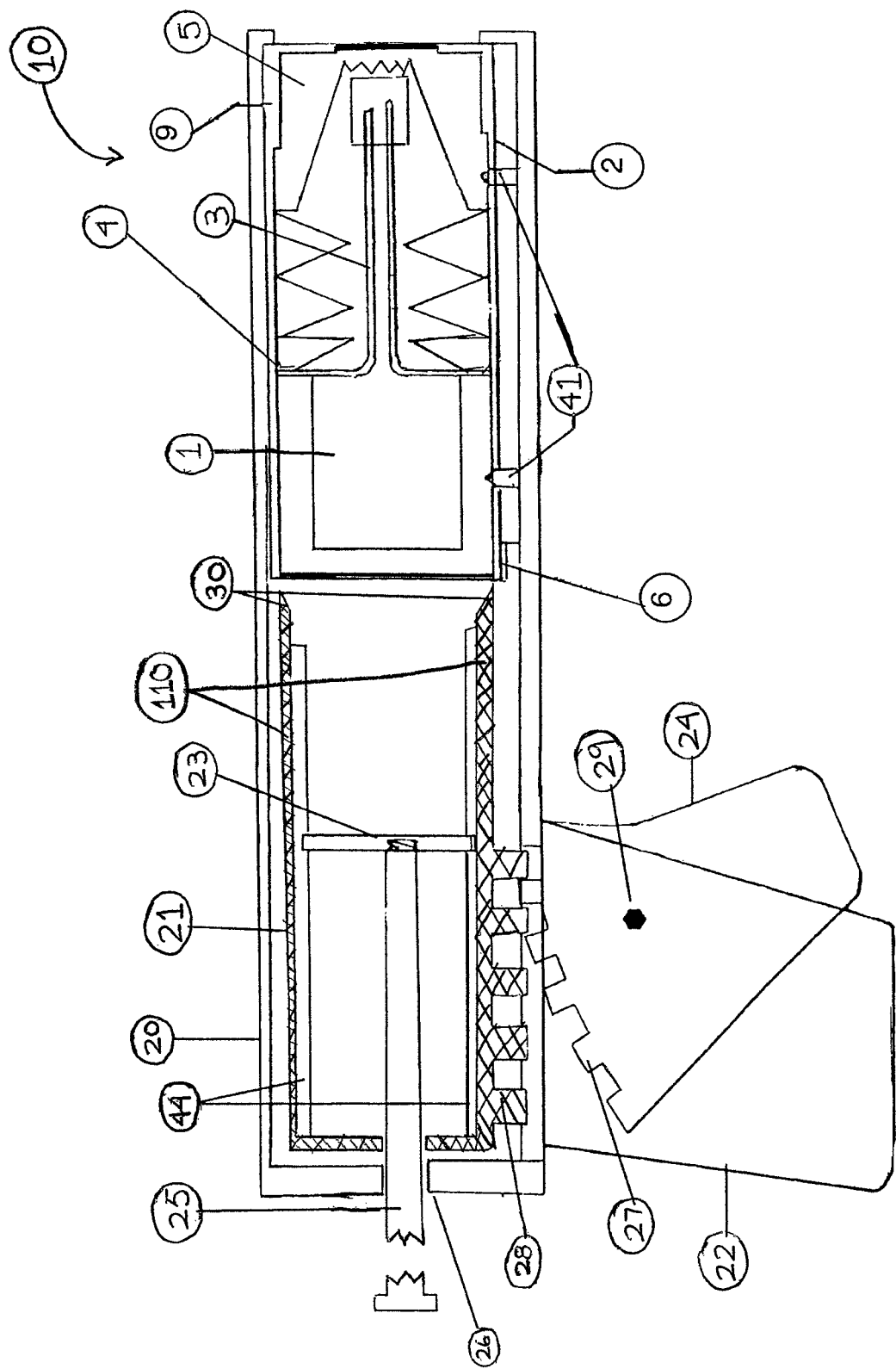
FIG. 2 is a side cross-sectional view of the cartridge of the continuous feed hypodermic syringe with self contained cartridge dispenser according to invention principles.

The continuous feed hypodermic syringe, in response to user actuation, causes a patient to be pierced with a needle and then injected with a predetermined medicinal dose that is contained in one of a plurality of sealed and sterile cartridges. There may be two mechanisms by which the device is actuated by a user. These different mechanisms will be discussed hereinafter with respect to FIGS. 2 and 3. FIG. 2 describes a mechanical geared actuation mechanism and FIG. 3 describes a spring-loaded actuation mechanism.

FIG. 2 is a side cross-sectional view of the cartridge of the continuous feed hypodermic syringe with self contained cartridge dispenser according to invention principles. The device includes a barrel 20 and a gripping member 22 connected to the barrel 20. The grip 22 includes a trigger 24 having a first set of gears 27 extending from an end thereof. The trigger 24 is connected to the grip 22 via a pivot 29. The delivery mechanism includes gears for mating with the gears 27 of the trigger 24. The mechanism is positioned substantially within the barrel 20 at an end opposite a cartridge area 10. The geared delivery mechanism includes a tube 21 having a second set of gears 28 which pairs with the first set of gears 27 upon depression of the trigger 24 and pivoting about pivot 29. This causes the geared delivery mechanism to move in a direction towards the cartridge area 10.

The tube 21 is positioned within and able to move along the length of the barrel 20. The tube 21 extends substantially along the length of the barrel 20 and adjacent to the cartridge area 10. The tube 21 has the second set of gears 28 formed integrally therein and, upon depression of the trigger, as discussed above, the gears cause the tube 21 to move within and along the length of the barrel 20 in a direction towards the cartridge area 10. The tube 21 includes a plurality of guide members 44 extending along a length thereof. A pressure plate 23 having a plurality of slots etched along the perimeter thereof is positioned within the tube 21. The slots on the pressure plate 23 receive a respective guide member enabling the plate to move along the length of the guide members 44.

An end of the tube 21 opposite the cartridge area 10 has an aperture extending therethrough permitting access to the tube 21. A plunger 25 extends through the aperture through center hole 26 and further through the tube 21 and is connected to the pressure plate 23. The force generated by actuating the trigger is transferred to a piston 110 which moves the pressure plate 23 along with the attached plunger 25. The piston 110 is shaded in the figure as a crosshatch pattern. The plunger 25 and pressure plate 23 only partially move forward, with the end of the plunger 25 still extended out of the hypodermic syringe. As the piston moves forward, the disinfectant (i.e., alcohol) contained within space/reservoir 5 is released. When the piston advances completely to the end, the disinfectant contained within space/reservoir 5 has all been dispensed. Also, the needle 3 has now extended beyond the membrane 7 and has pierced through the patient's skin. However, at this point, the medicine container 1 is still in tact and has not been dispensed. Next, the operator pushes in the remainder of the plunger 25 towards the direction of the needle inserted into the patient. This compresses the medicine container 1 and forces the medication out of the container through the needle and into the patient. The medication container is fully collapsed when the operator cannot move the plunger forward any further; this indicates that the entire content of the medication container has been emptied and dispersed into the patient. After the injection is complete, the operator pulls back the plunger all the way in a direction away from the patient. This permits the needle to retract out of the patient and back into the cartridge. The piston and tube 21 also moves back into the original location. Once the needle is no longer exposed, this indicates that the injection is complete and a new cartridge can be advanced onto position with the syringe.

The open end of the tube 21 has piercing edges 30. The piercing edges 30 facilitate penetration of the rear cap 6 of the cartridge in the cartridge area when the trigger 24 is depressed and the geared delivery mechanism is actuated. Once the cap has been pierced, the tube 21 continues to move into the cartridge area 10 and surrounds but does not apply any pressure to the flexible medication container 1. The tube 21 continues to move forward, reaching the collar of the needle and applies a force against the collar. The force of the tube 21 causes the container and the needle to move together. The spring 2 has a shoulder 8 formed integrally therewith and, the shoulder of the spring meets the stop 9 that is positioned within the interior circumference of the cartridge wall. This halts the movement of the spring. Unable to move further, the continuing pressure of the tube edge 30 on the spring 2 compress the spring 2. The compression however, does not fully collapse the spring. The spring 2 provides sufficient resistance to move the cutting tip 11 (FIG. 1) of the spring 2 forward and pierce the membrane 7. The design of the leading edge 11 of the spring spreads this membrane so as not to contaminate the needle that will emerge and also permits the disinfectant/alcohol to be released onto the needle 3 and the area of the patient to be pierced, as described above. Positioning ball bearings 41 may be utilized as sprocket guides.

Figure 3:
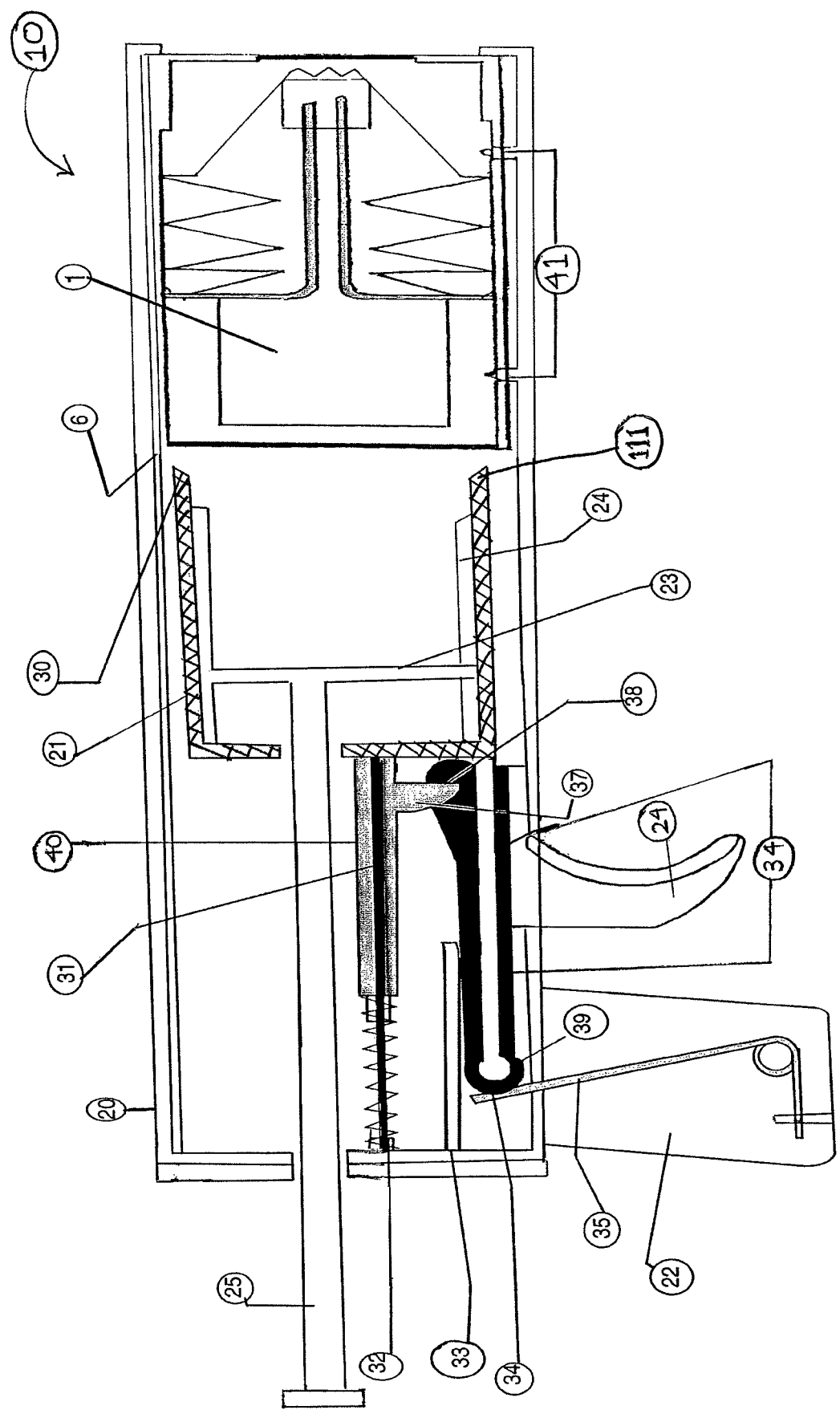
FIG. 3 is a side cross-sectional view of the continuous feed hypodermic syringe with self contained cartridge dispenser according to invention principles.

FIG. 3 is a side cross-sectional view of the continuous feed hypodermic syringe with self contained cartridge dispenser according to invention principles. FIG. 3 shows an additional delivery mechanism for injecting a patient with the medication in a cartridge. Shown herein the trigger 24 is not formed integrally with the gripping member 22. The trigger 24 is connected to and extends dorsally from the barrel 20 and positioned between the gripping member 22 and the cartridge area 10. The trigger 24 is connected to a shaped spring 34 having a flange 39 at a rear end thereof. All components of the spring-loaded delivery mechanism not otherwise described are positioned within the barrel 20 of the device. The shaped spring 34 further includes a slot 38 able to receive a cog 37 which will be discussed below. The gripping member 22 includes a compression spring 38 anchored at a base thereof. The flange 39 of the shaped spring 34 contacts an end of the compression spring 35 opposite the anchor and is able to selectively compress the compression spring 35 upon actuation of the trigger 24. A depressing bar 33 lies above the flange 39. A piston 111 is shown shaded in as a crosshatch pattern.

The device further includes a spring rod 40 having a cog 37 extending from an edge thereof. The cog 37 may be selectively received by the cog slot 38. The spring rod 40 is positioned on a rod guide 31. An actuation spring 32 is positioned on the rod guide 31 and is connected between an end of the rod 40 opposite the cog 37 and an inner rear wall of the barrel 20. A sprocket guide 41 is shown in FIG. 3.

When a trigger 24 is pulled, the shaped spring 34 is caused to move in a direction opposite the cartridge area 10 and the flange 39 of the shaped spring 34 compresses the compression spring 35. Additionally, movement of the shaped spring 34 causes the spring rod 40, which is releaseably connected to the shaped spring 34 via the cog 37, to compress the actuation spring 32 between the spring rod 40 and the rear wall of the barrel. The flange 39 compresses the compression spring 35 and releases the cog 37 attached to rod 40 from the cog slot 38. The actuation spring 32, which has been fully compressed, is released causing the spring rod 40 to move in a direction towards the cartridge area 10 and contact the rear end of the tube 21. The decompression force is transferred to the tube 21 and the cutting edge 30 of the tube 21 penetrates the rear end cap 6. Upon penetration of the rear membrane 6, the operation of the device resulting in injection of medicine is the same as described above with respect to FIG. 2.

Figure 4:
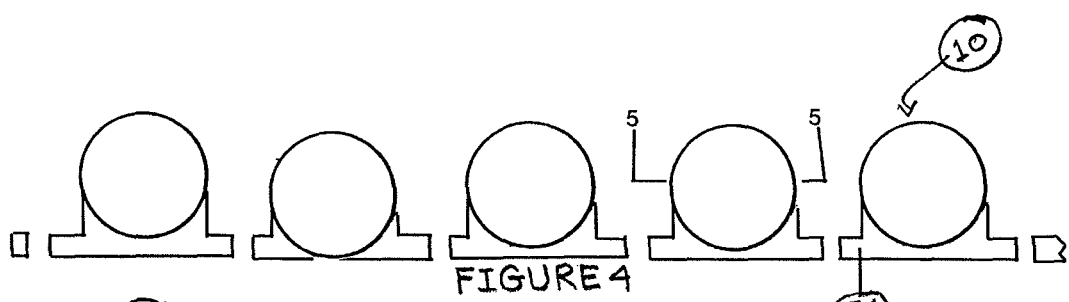
FIG. 4 is an end view of a clip that retains the cartridges shown in FIG. 1 for use with the continuous feed hypodermic syringe according to invention principles.
Figure 5:
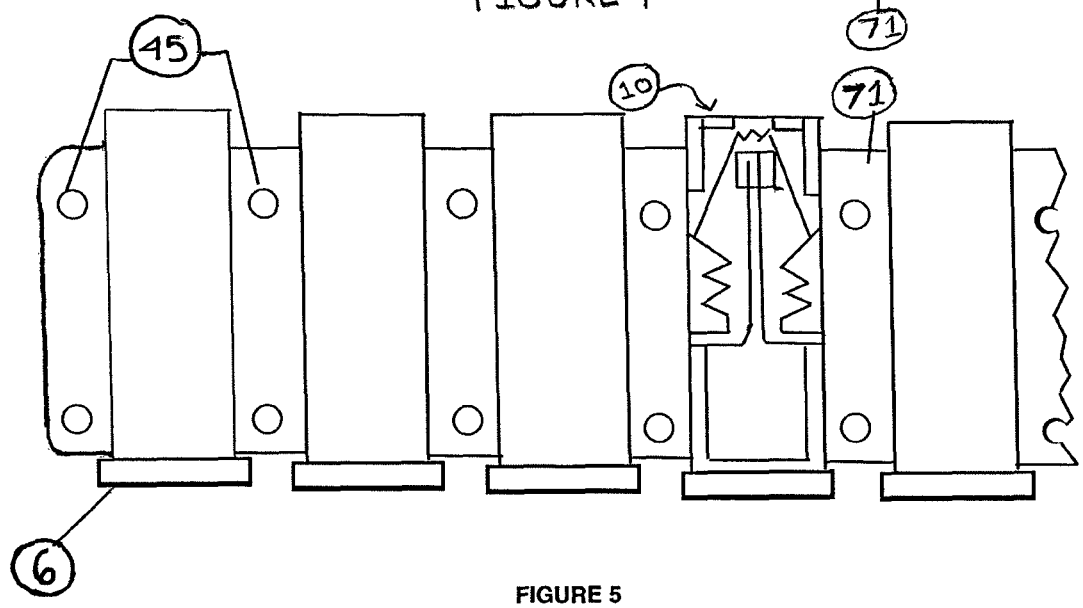
FIG. 5 is a top view with a partial cross-sectional view taken along the line labeled 5-5 in FIG. 4 of the clip used with the continuous feed hypodermic syringe according to invention principles.

FIG. 4 is an end side view of a clip 71 that retains the cartridges shown in FIG. 1 for use with the continuous feed hypodermic syringe according to invention principles. A plurality of cartridges is shown attached to clips. Each cartridge 10 contains liquid to be dispensed to a patient and includes the features shown and discussed above with respect to FIG. 1. The cartridges are positioned on the clip 71 and may be fed through the dispenser to quickly and efficiently dispense the liquids contained in the cartridges. Each cartridge is self contained and factory loaded, packed and sterilized. The cartridges, as shown herein, are capped 6 at the rear by a circular ring and covered by a thin membrane. Sprocket holes 45 and end caps 6 are shown in FIG. 5. Alternatively, a flexible belt may be used instead of a clip.

FIG. 5 is a top view with a partial cross-sectional view taken along the line labeled 5-5 in FIG. 4 of the clip 71 used with the continuous feed hypodermic syringe according to invention principles. The clip may be manufactured with the cartridges as part of the clip by injection molding for purposes of economy as well as reducing error although other manufacturing methods may be used. The clip includes sprocket guides between the cartridges that may be at least one of apertures and notches that mate with matching protrusions such as spring loaded ball bearings positioned within the cartridge area of the barrel of the device. The spring loaded ball bearings function as guides for securing the cartridge to the clip. The guides indicate when the cartridge is in proper position with a click or slight pressure that will be felt as the ball bearings are received with in the at least one of holes and notches. The clip may include any number of cartridges. The clip has also been designed so that it may be inserted correctly into the opening ports in the syringe from either the left or right side but cannot be inserted in a reversed or backward position.

Because the clip may be preformed with the cartridges attached thereto, a clip may contain cartridges having the same medication and dosage level which may facilitate rapid vaccination of patients at different times during the course of a day. For example, children who need vaccinations for school can be vaccinated without preparing separate syringes for each child but, because the cartridges are sterile, all the vaccinations need not occur concurrently or in rapid succession. Alternatively, if a treatment regime for a disease requires multiple, sequential and/or successive injections of different medications, the clip may include cartridges having the different medications and dosages of each medication as required by the treatment. This ensures that the patient has the proper sequence and dosages of medications that are required to treat the disease.

Figure 6:
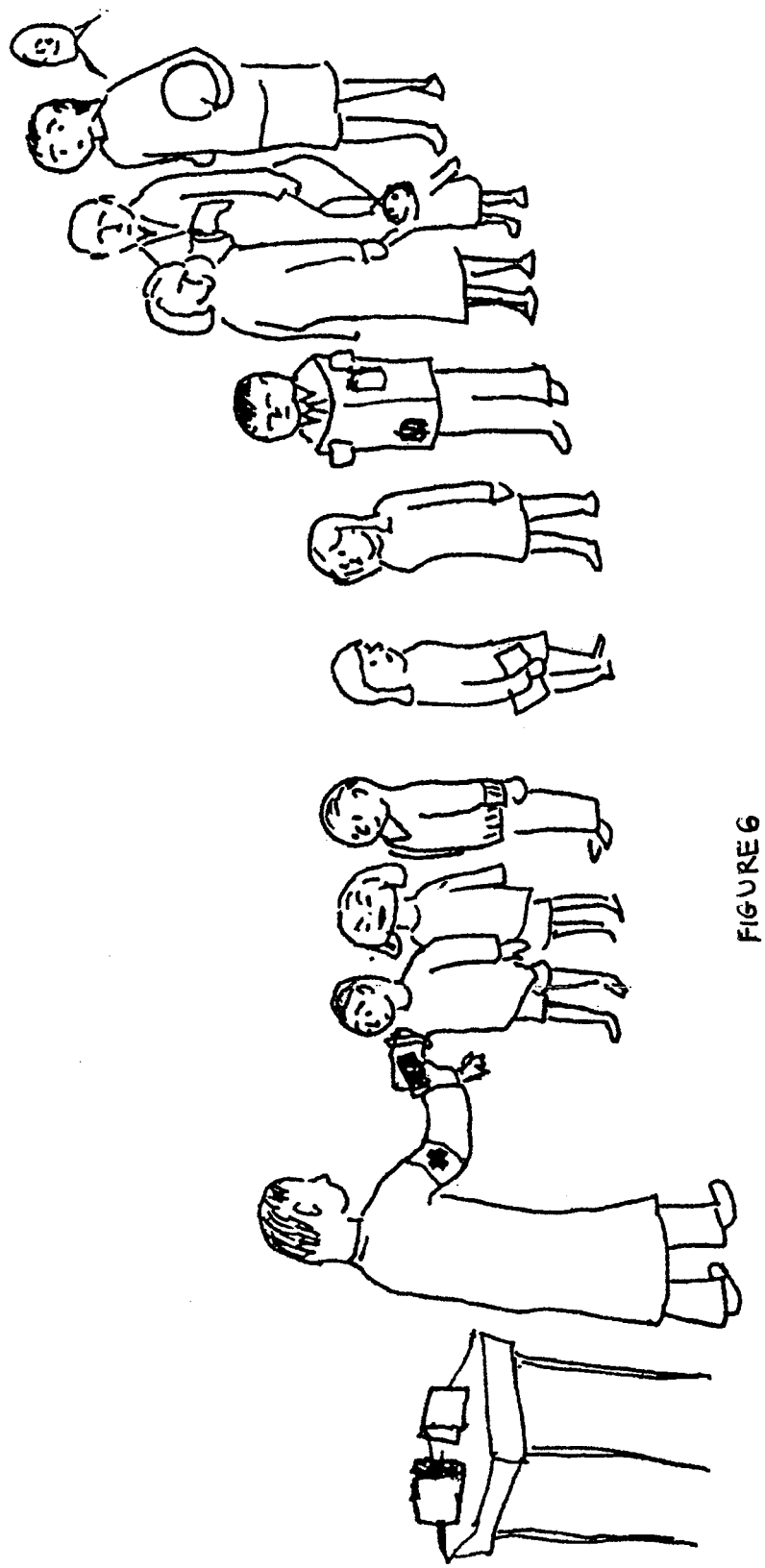
FIG. 6 is an illustrative view of the continuous feed hypodermic syringe being used to inject a large number of patients according to invention principles.
Figure 7:
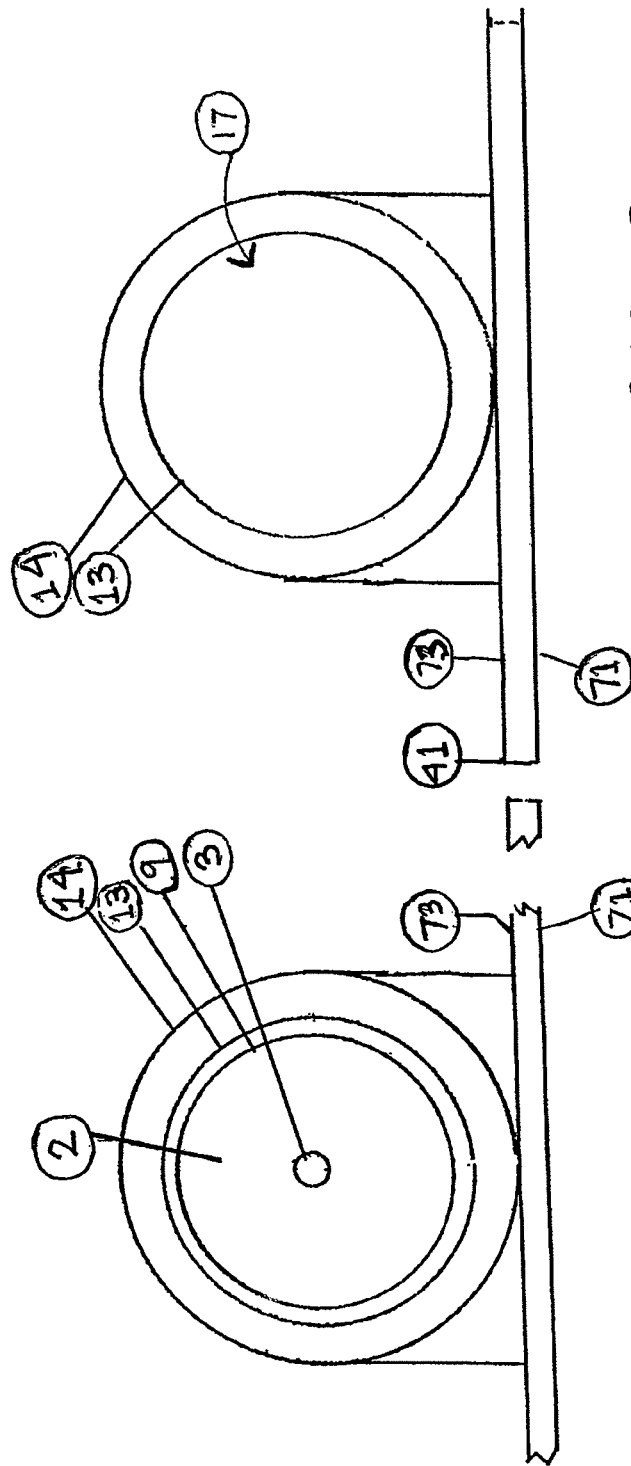
FIG. 7A is a front end view of the medicament cartridge used with the continuous feed hypodermic syringe according to invention principles.
FIG. 7B is a rear end view of the medicament cartridge used with the continuous feed hypodermic syringe according to invention principles.

FIG. 6 is an illustrative view of the continuous feed hypodermic syringe being used to inject a large number of patients according to invention principles. A caregiver administers a vaccine to a patient using the dispenser. After the patient receives the vaccine, the dispenser is then immediately reloaded with another cartridge for inoculating another patient by the caregivers pulling or pushing on the clip so that the next adjacent unused cartridge is loaded into the dispenser. The dispenser provides for rapid deployment of vaccination to a large population with little effort. The dispenser further maintains a sterile environment during successive vaccinations reducing the transmission of any disease from patient to patient.

FIG. 7A is a front end view of the medicament cartridge used with the continuous feed hypodermic syringe according to invention principles. The cartridge 10 is secured to the clip 71 by securing members 73 which maintain the position of the cartridge 10 during the injection process. The cartridge 10 is circular in shape and includes an outer wall 14 and an inner wall 13. A shoulder stop 9 is positioned on the inner wall 13 and at the front most end of the cartridge 10. As discussed above, the shoulder stop 9 stops the movement of the spring 2 to allow the needle 3 to penetrate the sealing membrane shown in FIGS. 1-5.

FIG. 7B is a rear end view of the medicament cartridge used with the continuous feed hypodermic syringe according to invention principles. The rear end of the cartridge 10 shows the outer wall 14 and inner wall 13. The container for retaining medication is positioned within the inner wall 13 and is sealed by sealing membrane 17.

Figure 8:
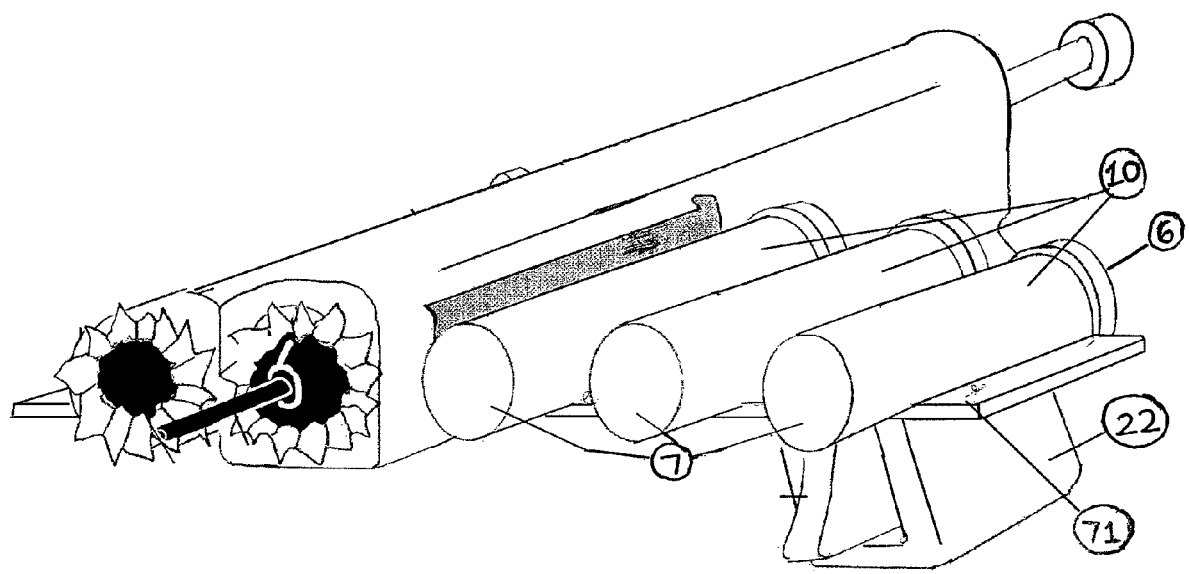
FIG. 8 is an isometric view of the continuous feed hypodermic syringe in use according to invention principles.

FIG. 8 is an isometric view of the continuous feed hypodermic syringe in use according to invention principles. When the device is actuated as described above with respect to FIGS. 2 and 3, the needle penetrates the membrane at the front end thereof and spreads the membrane in an outward and open pattern. The spring is compressed and the needle is caused to extend outward from the barrel of the device. The needle penetrates the skin of the patient and the medicine in the container is forced out through the needle and into the patient. FIG. 8 shows how the device facilitates multiple quick injections of patients using a device that may receive a plurality of individual medicament cartridges. After the medicine is dispensed, the plunger is pulled back so as to allow withdrawal of the needle back into the cartridge and reset the trigger mechanism. The clip is then pulled to remove the spent cartridge and load the adjacent unused cartridge.

Figure 9:
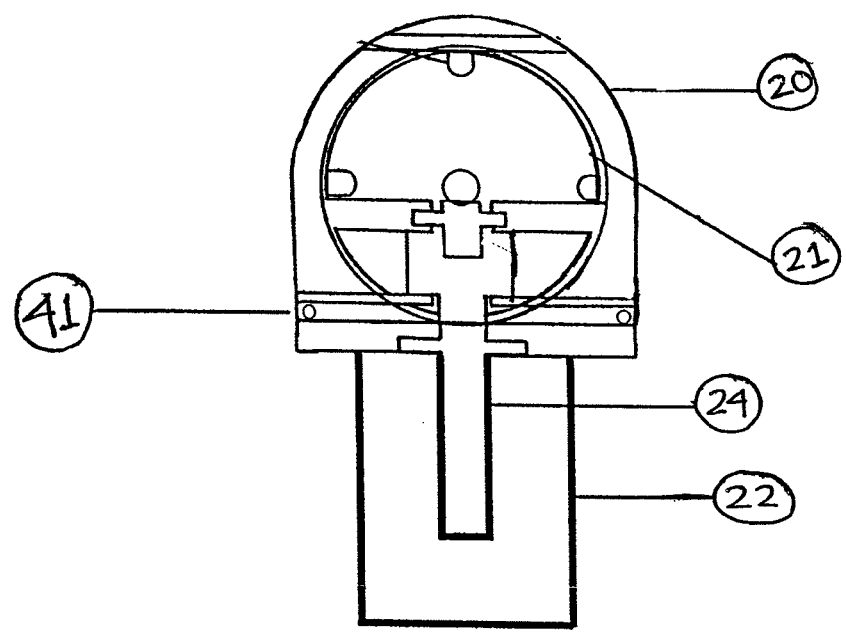
FIG. 9 is a front end view of the barrel of the continuous feed hypodermic syringe according to invention principles.
Figure 10:
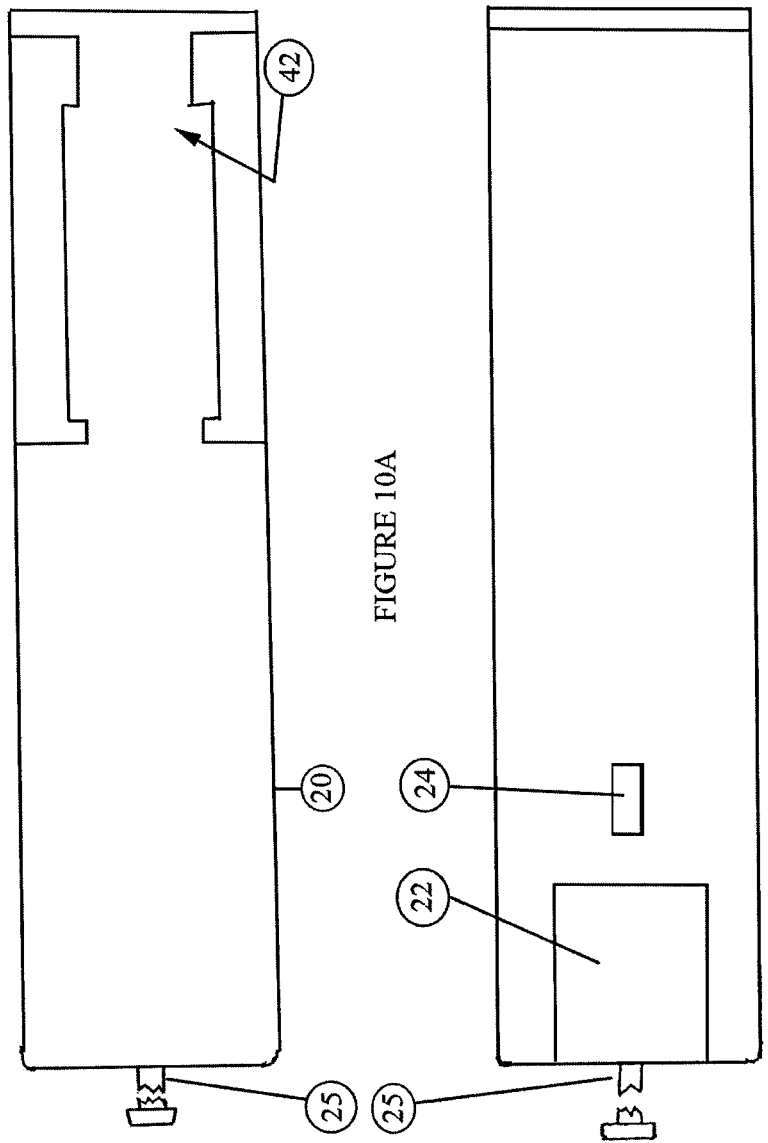
FIG. 10A is a top view of the barrel of the continuous feed hypodermic syringe according to invention principles.
FIG. 10B is a bottom view of the barrel of the continuous feed hypodermic syringe according to invention principles.

FIG. 9 is a front end view of the barrel of the continuous feed hypodermic syringe of FIG. 3 without a loaded cartridge according to invention principles. This figure details the spring loaded delivery mechanism described above with respect to FIG. 3.

FIG. 10A is a top view of the barrel of the continuous feed hypodermic syringe according to invention principles. The top view of the barrel shows the cartridge port 42 that selectively receives an individual medicament cartridge containing medicine that is to be injected into the patient. After the contents of each cartridge is expelled, a new cartridge is moved in to the cartridge port enabling a user to inject the medication into a different patient.

FIG. 10B is a bottom view of the barrel of the continuous feed hypodermic syringe according to invention principles. The bottom of the barrel of the device includes the gripping member 22 and the trigger mechanism 24. While the trigger 24 is shown separately from the gripping member 22, it is contemplated that they be formed together such as described in FIG. 2.

Figure 11:
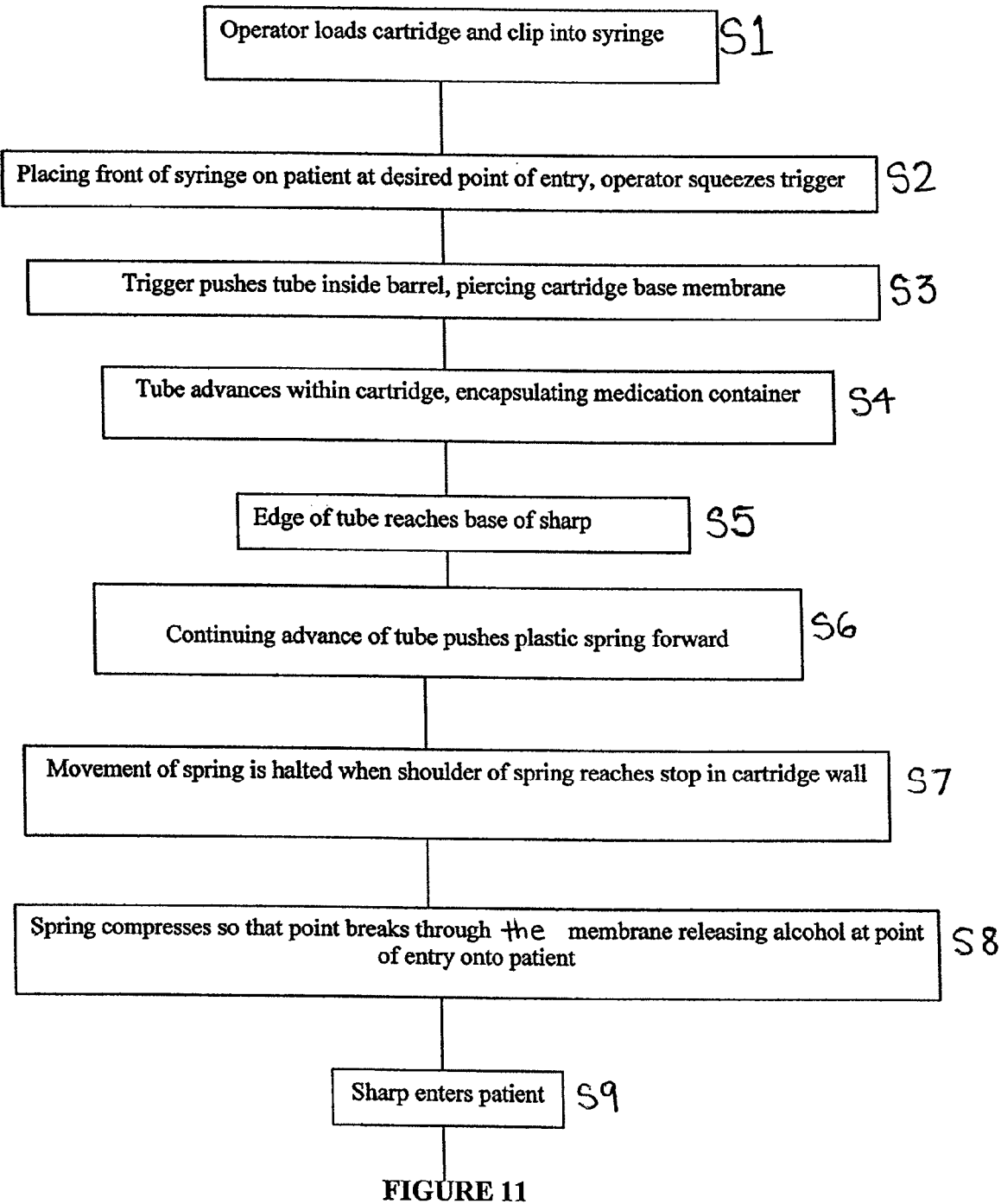
FIG. 11 is a flow diagram describing operation of the continuous feed hypodermic syringe with self contained cartridge dispenser according to invention principles.
Figure 12:
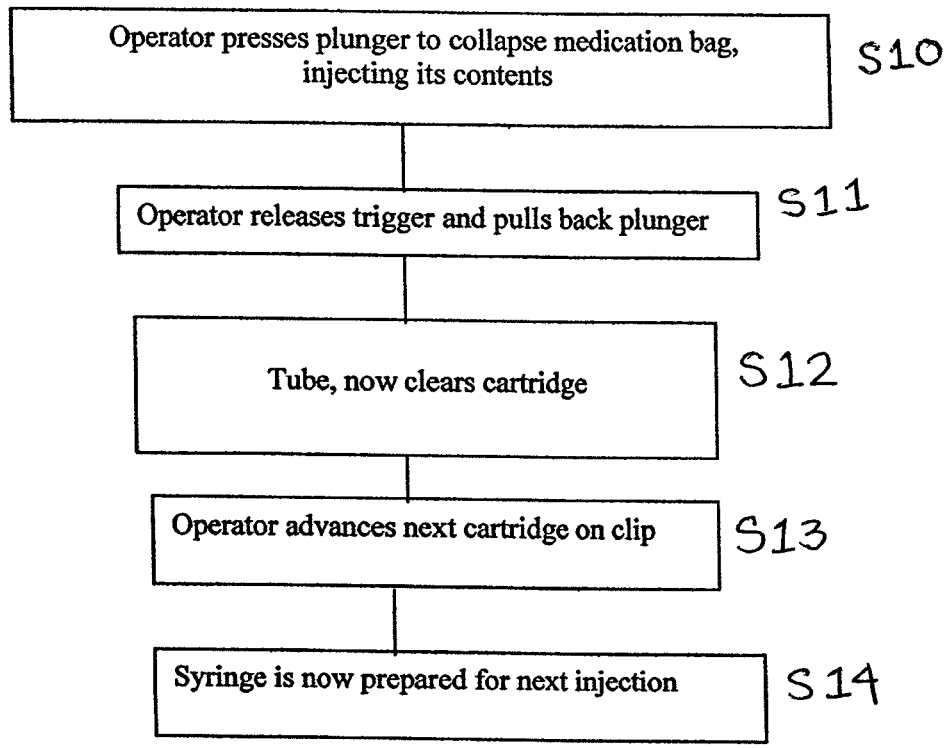
FIG. 12 is a flow diagram of the operation of the continuous feed hypodermic syringe continued from FIG. 11 according to invention principles.

FIGS. 11 and 12 describe the operation of the continuous feed hypodermic syringe with self contained cartridge dispenser according to invention principles. The operator of the device loads the cartridge that is on a clip into the cartridge port of the barrel of the device, shown in step S1. The open end of the barrel is selectively positioned by the operator directly over the area on the patient to be injected and the trigger is depressed by the operator initiating the delivery mechanism, shown in step S2. The delivery mechanism is described hereinabove with respect to FIGS. 2 and 3. The delivery mechanism causes a tube inside the barrel of the device to pierce a rear membrane on the cartridge, shown in step S3. The tube advances and surrounds the cartridge, shown in step S4 until the edge of the tube contacts the base of the needle, shown in step S5. Further movement of the tube moves the spring within the cartridge and that surrounds the needle, shown in step S6. The shoulder of the spring reaches a stop that is positioned within the inner wall of the cartridge stopping the movement of the spring, shown in step S7 and resulting in compression of the spring. The leading edge of the spring and needle penetrates the membrane that seals the front edge of the cartridge. A disinfectant stored between the membrane the needle is applied to the skin surface of the patient prior to insertion of the needle and the needle is inserted into the patient as shown in step S8. Upon injection into the patient, shown in step S9, the operator moves the plunger in a direction towards the patient to collapse the container within the cartridge that includes the medicine, shown in step S10. The medicine is forced through the needle and into the patient. The operator releases the trigger and moves the plunger in a direction away from the patient to reset the delivery mechanism, shown in step S11. The needle is withdrawn back into the cartridge, shown in step S12 and the operator may selectively advance the clip to remove the spent cartridge and insert an unused cartridge into the barrel of the device, shown in steps S13 and S14.

Figure 13:
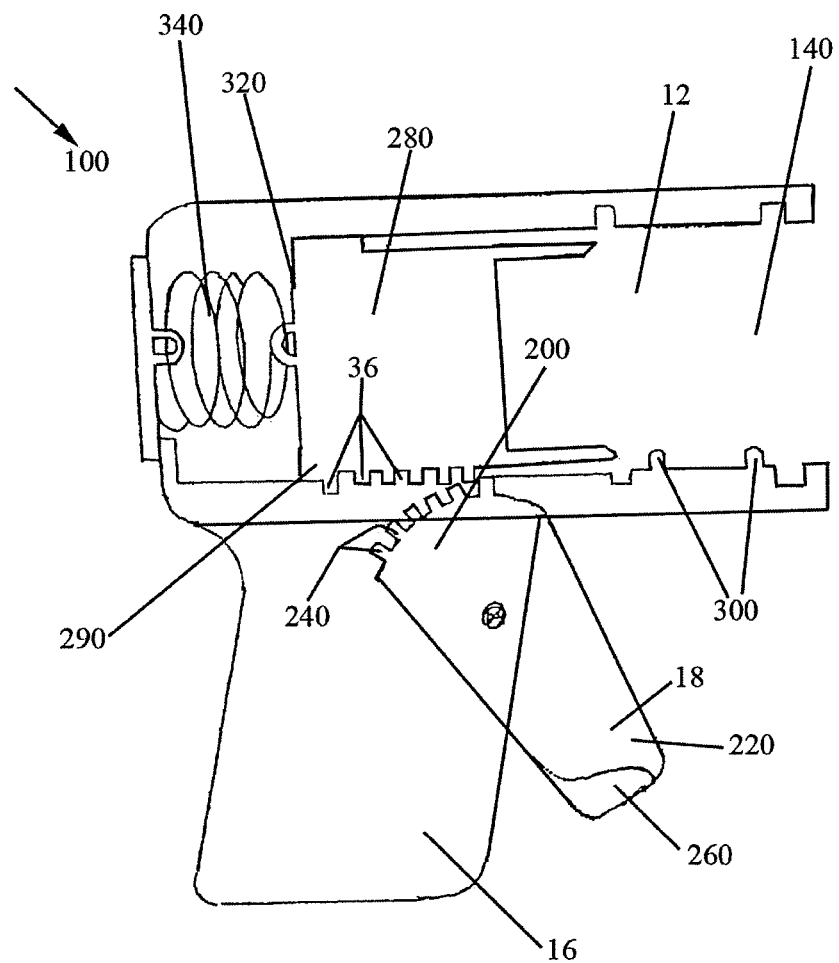
FIG. 13 is a side cross-sectional view of the continuous feed hypodermic syringe dispenser with feed clip according to an additional embodiment of the invention principles.
Figure 15:
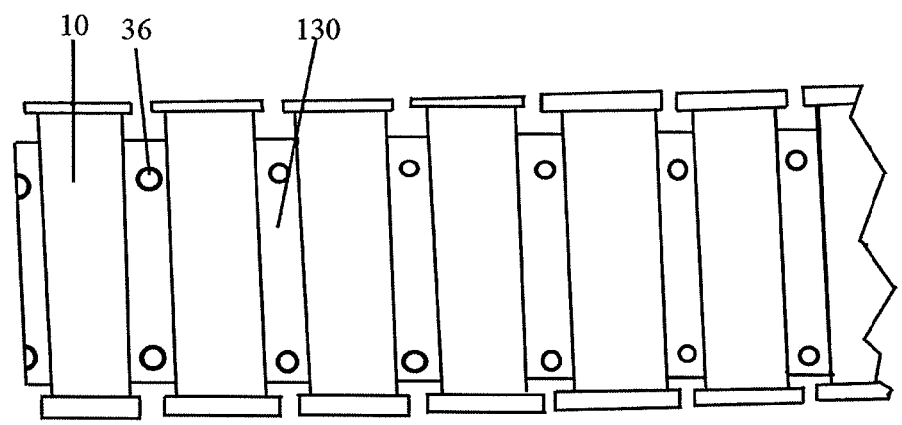
FIG. 15 is a top cross-sectional view of the feed clip of the continuous feed hypodermic syringe dispenser with feed clip according to invention principles.

FIG. 13 is a side view of the continuous feed hypodermic syringe dispenser 100, according to an alternate embodiment. The cartridges 10 (shown in FIG. 19) are snapped onto a clip 130 (shown in FIG. 19), which is inserted into a barrel 12 of the dispenser near a mouth 140 of the barrel 12. The clip 130 includes a plurality of gears/sprockets 36 as shown in FIG. 15. The barrel 12 includes a plurality of spring mounted protrusions 300 for being received by the plurality of holes in the clip 130, to align the clip 130 and maintain the clip 130 in the appropriate position. The dispenser includes a handle 16 having a trigger 18. The trigger 18 has a first end 200 and a second end 220, opposite therefrom. The first end 200 of the trigger 18 includes a plurality of sprockets 240. The second end 220 of the trigger 18 includes a notch 260 for aiding an operator in the movement of the trigger 18. The notch 260 aids the user in manually moving the trigger 18 back into the firing position should the trigger get stuck in the spent position and not return. The barrel 12 further houses a piston 280, having a base 290 and a rear end 320. The rear end 320 of the piston is fastened to a compression spring 340. The base 290 of the piston has a plurality of sprockets 36, which are engaged by the matching sprockets 240 on the trigger 18. In use, when the trigger 18 is squeezed and thereby pivoted, the sprockets 240 on the trigger 18 engage the matching sprockets 36 in the piston 280 and cause the piston 280 to advance. When the piston 280 is forced forward, the spring 340 is stretched and the trigger and thus the piston 280 engages the cartridge (shown in FIG. 19), causing the liquid or vaccine to be dispensed therefrom. Upon release of the pressure on the piston 280, the spring 340 pulls the piston 280 back into position for a new injection and the engagement of the sprockets 240 and 36 cause the trigger 18 to return to an activation position.

Figure 14:
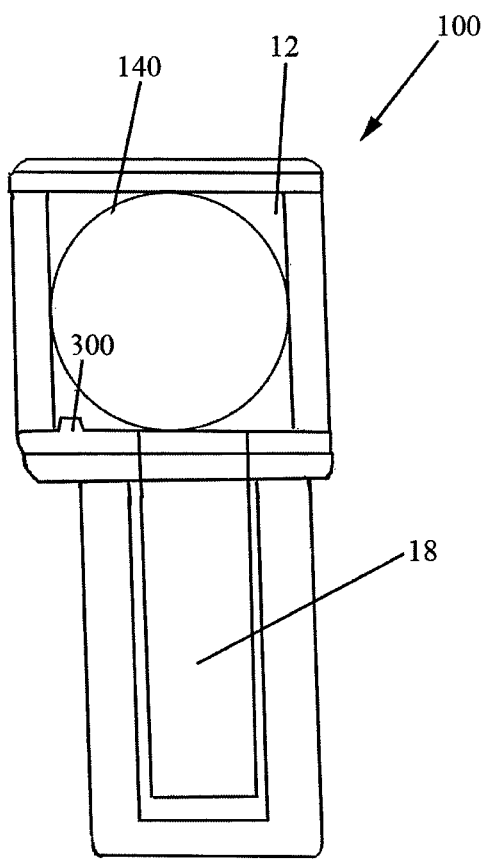
FIG. 14 is a front view of the continuous feed hypodermic syringe dispenser with feed clip according to invention principles.

FIG. 14 is a front view of the continuous feed hypodermic syringe dispenser 100. The cartridge 10 is loaded in the barrel 12 of the dispenser 100, near the mouth 140 of the barrel 12. The cartridges 10 are snapped onto the clip 130. When the cartridge 10 has been used, the operator pulls the clip 130 through the barrel 12 releasing the protrusions from their position with in the holes surrounding the spent cartridge and until the holes in the clip 130 receive respective protrusions 300 surrounding an adjacent cartridge in the barrel 12, indicating that the new cartridge 10 is aligned with the piston 280 and in position for use in the next injection.

FIG. 15 is a top view of the feed clip of the continuous feed hypodermic syringe dispenser 100. Each cartridge 10 may have a plurality of arrow shaped protrusions on four sides. The clip 130 may have a similar shaped indentation to match each cartridge protrusion. Alternatively, the protrusions may be any other geometric shape able to be received by a corresponding recess in the clip and retain the cartridge in position. In use, when the male and female protrusions on the cartridge 10 and clip 130 mate, the cartridge 10 is secured to the clip and prevented from being set on the clip 130 in the wrong direction. The clip 130 also includes sprockets 36 or indentations surrounding each cartridge 10. The clip 130 is inserted into the barrel 12 near the mouth 140 of the barrel 12 from one side. The clip 130 is positioned so that when inserted, spring loaded protrusions 300 in the barrel 12 engage the matching sprockets 36 in the clip 130 surrounding a cartridge 10. The engagement of the loaded protrusions 300 and matching indentations 36 cause the cartridge 10 to be aligned within the barrel 12.

Figure 16:
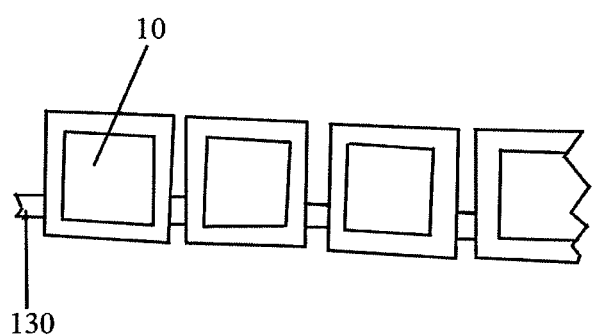
FIG. 16 is an end view of the continuous feed hypodermic syringe dispenser with feed clip according to invention principles.

FIG. 16 is a view of the feed clip 130 of the continuous feed hypodermic syringe dispenser 100 including the plurality of cartridges 10 connected thereto.

Figure 17:
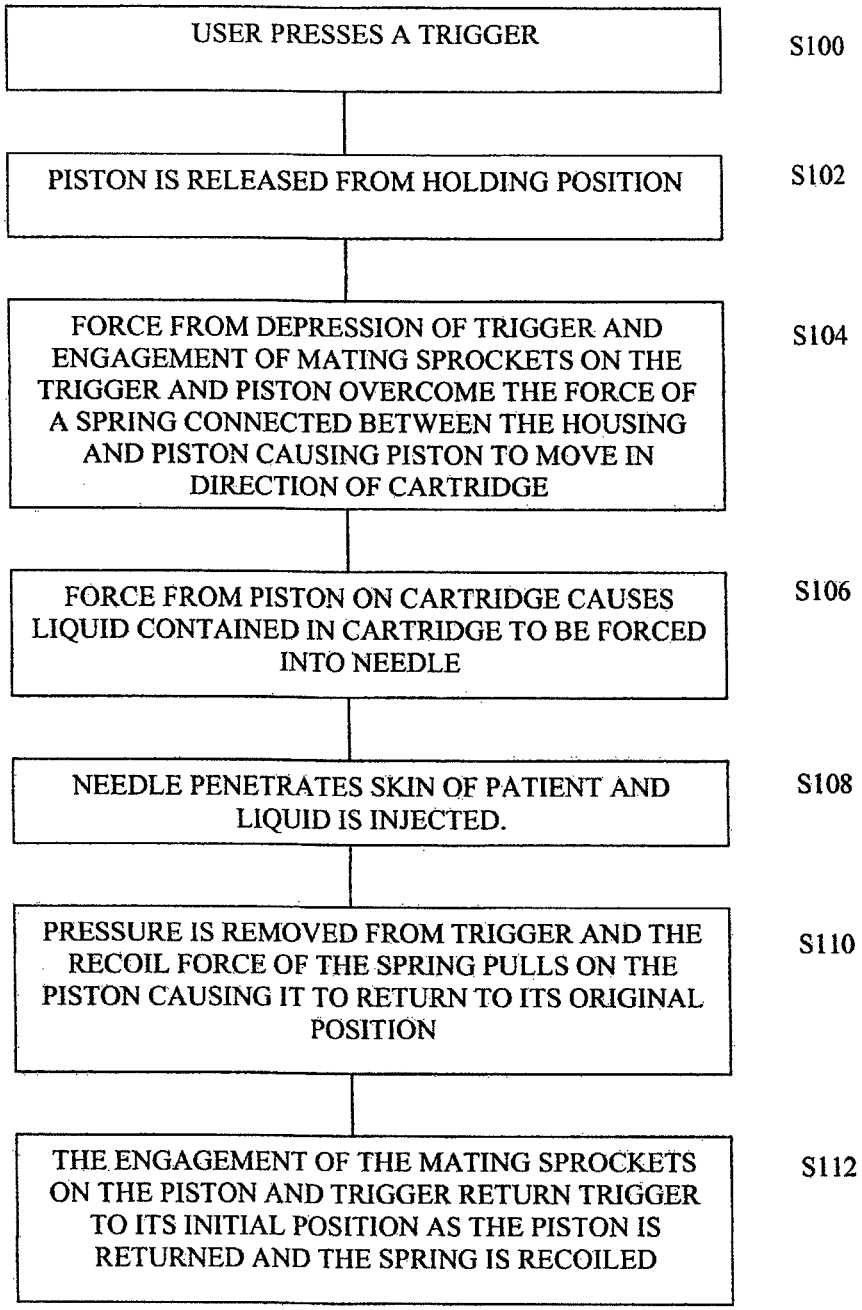
FIG. 17 is a flow diagram describing use of the continuous feed hypodermic syringe dispenser with feed clip according to invention principles.

FIG. 17 is a flow diagram describing the dispensation of the vaccine using the continuous feed hypodermic syringe shown in FIG. 13. The user depresses a trigger and releases a piston from a holding position in steps S100 and S102. The force from a depression of the trigger and engagement of the mating sprockets on the trigger and piston overcome the force of a spring connected between the housing and piston causing the piston to travel along the length of the barrel in a direction towards a cartridge contained therein in step S104. In step S106, upon contact with the cartridge, the force exerted by the movable piston causes the vaccine to travel through a needle. The needle penetrates the skin of the user and the user is vaccinated and receives the medication in step S108. Once pressure is removed from the trigger, the recoil force of the spring pulls on the piston causing it to return to its original position as stated in step S110. The engagement of the mating sprockets on the piston and trigger return the trigger to its initial position as the spring recoils returning the piston to its initial position as discussed in step S112.

Figure 18:
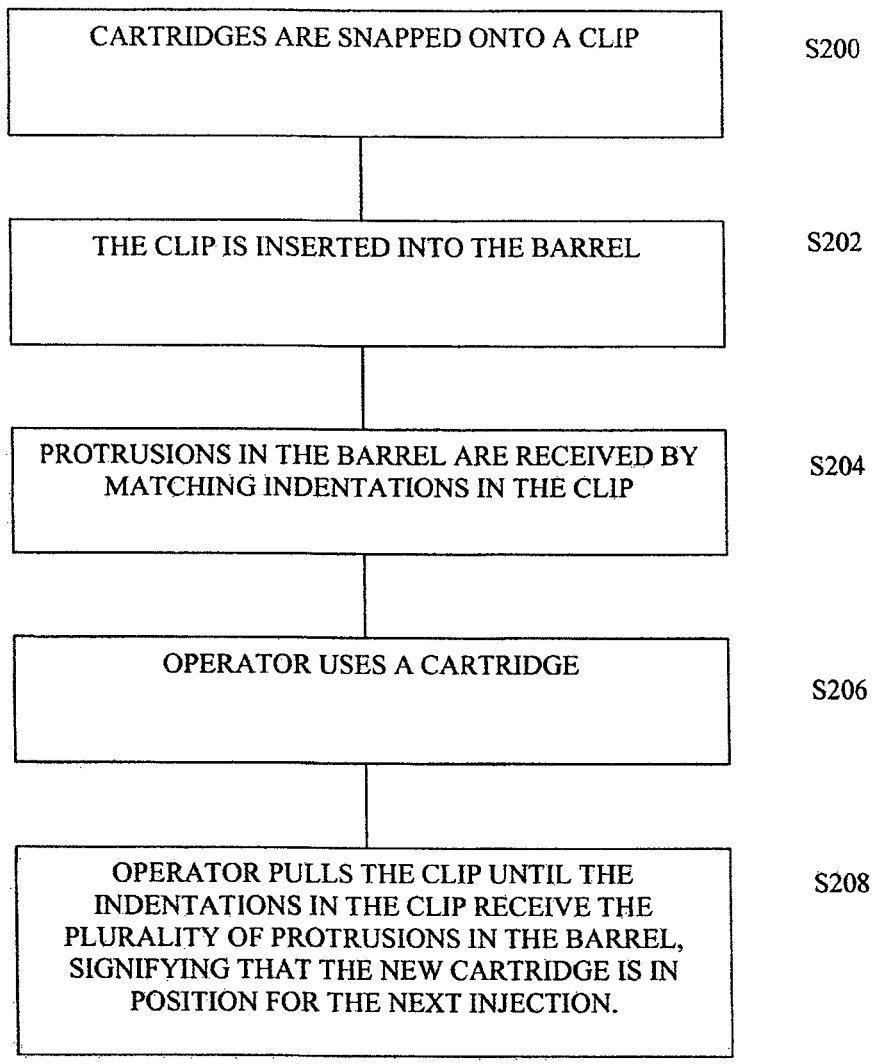
FIG. 18 is a flow diagram describing continuous loading of cartridges in the continuous feed hypodermic dispenser with feed clip according to invention principles.

FIG. 18 is a flow diagram describing the process of reloading the continuous feed hypodermic syringe dispenser. The cartridges are snapped onto a clip in step S200. In step S202, the clip is inserted into the barrel of the dispenser. Protrusions in the barrel are received by matching indentations in the clip in step S204. In step S206 the operator uses a cartridge as discussed herein. In step S208, the operator pulls the clip until the spent cartridge is removed and the indentations in the clip surrounding an adjacent cartridge are received in the plurality of protrusions in the barrel, signifying that the new cartridge is in position for the next injection. This process is repeated for dispensing the contents of each subsequent cartridge.

Figure 19:
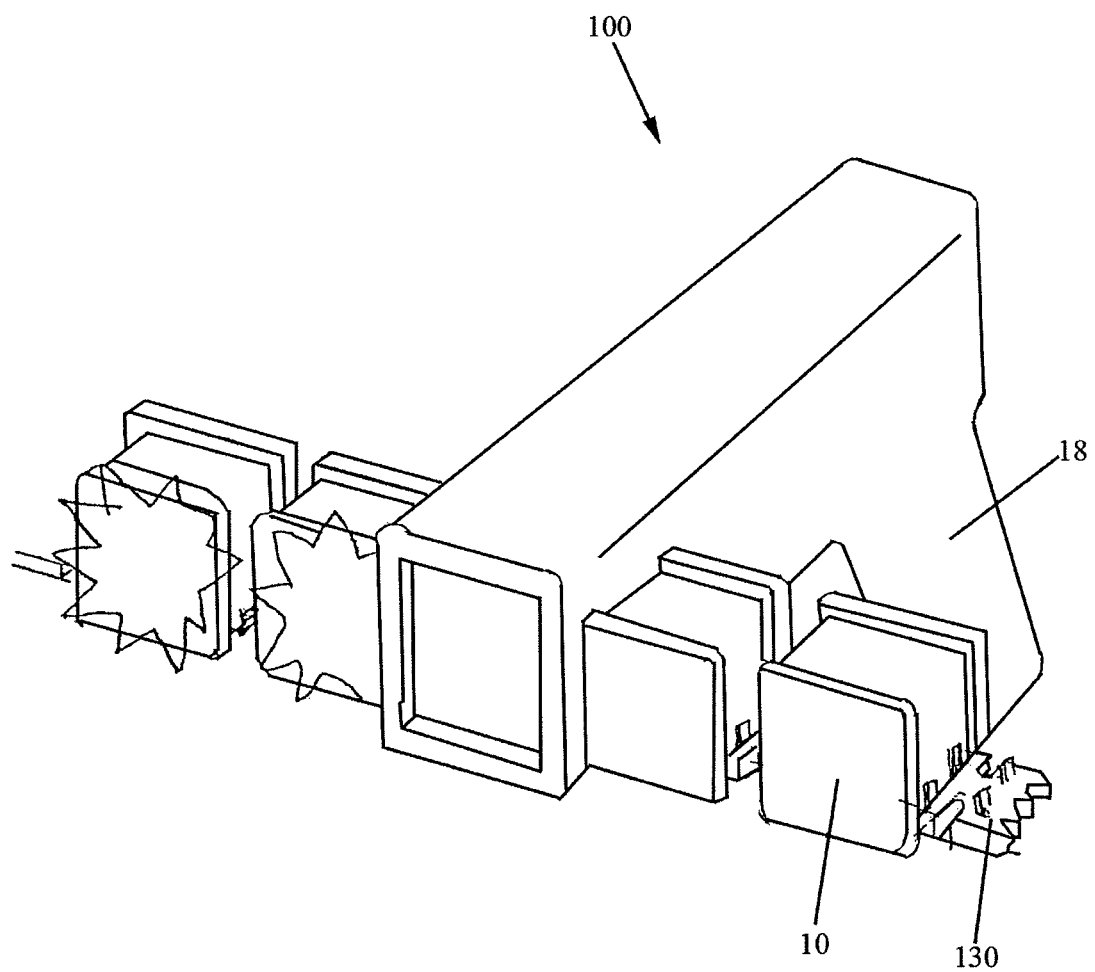
FIG. 19 is a perspective view of the continuous feed hypodermic syringe dispenser with feed clip according to invention principles.

FIG. 19 is a perspective view of the continuous feed hypodermic syringe dispenser 100 with feed clip 130. The plurality of cartridges 10, having a square shape, is shown attached to the clip 130. Each cartridge 10 contains liquid to be dispensed to a patient. The cartridges 10 are fed through the dispenser 100 to quickly and efficiently dispense the liquids contained in the cartridges 10. The dispenser 100 automatically and continuously dispenses a vaccine contained in one of a plurality of cartridges 10 using the trigger to actuate the piston that extends through the hollow barrel of the dispenser as described previously. An end of the piston contacts a rear edge of the cartridge 10 forcing the vaccine to flow through the needle for insertion into a patient. Upon completion of the vaccination, the spring pulls the piston back into position for a new injection and at the same time returning the trigger to the activation position.

Figure 20:
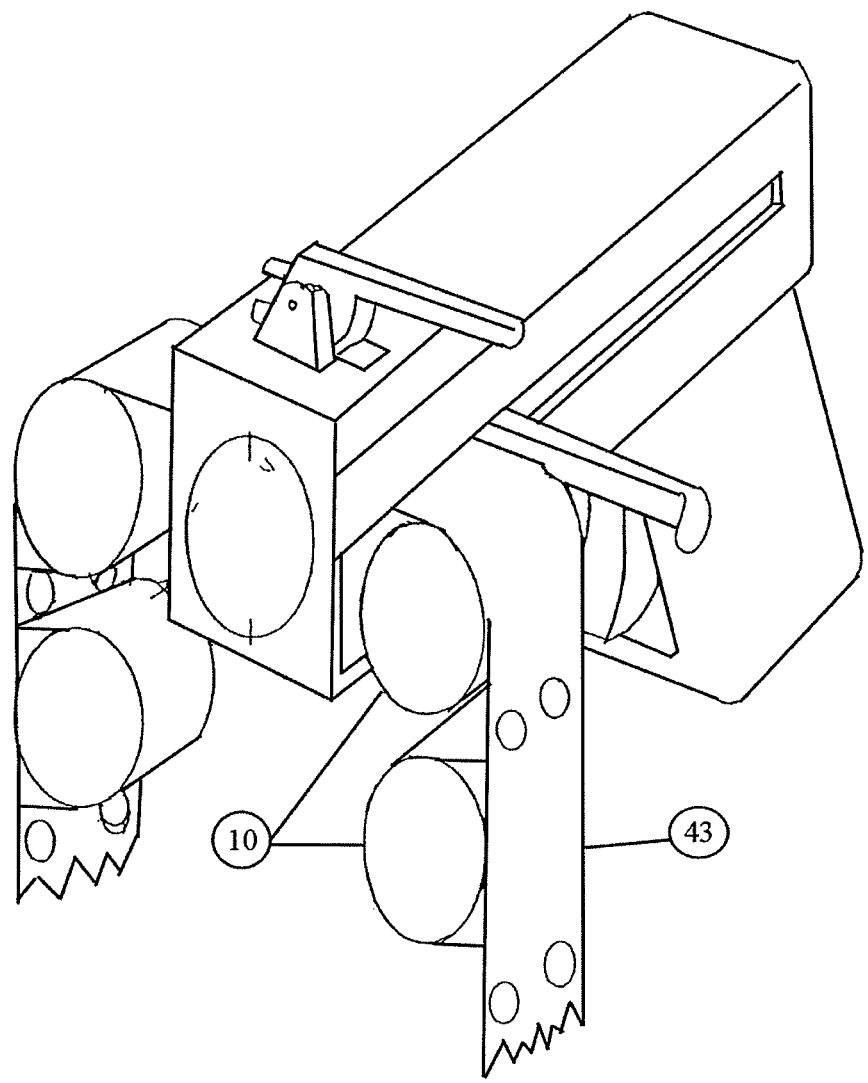
FIG. 20 is a perspective view of the continuous feed hypodermic syringe with self contained cartridge dispenser according to an additional embodiment of the invention principles.

FIG. 20 is a perspective view of the continuous feed hypodermic syringe with self contained cartridge dispenser, according to a further embodiment. A plurality of cartridges 10 is shown attached to a flexible belt 43. Each cartridge contains liquid to be dispensed to a patient. The cartridges are fed through the dispenser to quickly and efficiently dispense the liquids contained in the cartridges. The dispenser automatically and continuously dispenses a vaccine contained in one of a plurality of cartridges using a lever to actuate a piston that extends through a hollow barrel. An end of the piston contacts a rear edge of the cartridge and causes a needle to extend therefrom for insertion into a patient. Upon completion of the vaccination, a handle extending laterally outward from the barrel and connected to the piston is moveable to withdraw the piston from contact with the rear end of the cartridge thereby drawing the needle back into the cartridge. The movement of the handle causes a gear tooth within the barrel to rotate and engage a sprocket hole extending through the belt. The rotation causes the belt to move in at least one of a clockwise or counterclockwise direction and remove the spent cartridge from the barrel and replace the spent cartridge with an unused cartridge for injection of a further patient.

Figure 21:
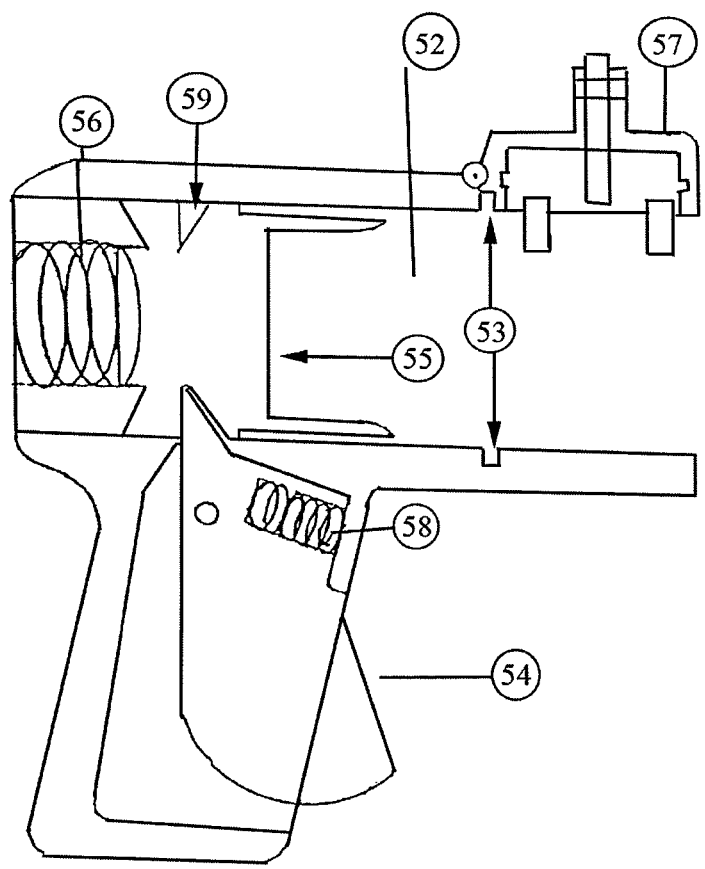
FIG. 21 is a side cross-sectional view of the continuous feed hypodermic syringe with self contained cartridge dispenser according to invention principles.

FIG. 21 is a side view of the continuous feed hypodermic syringe with self contained cartridge dispenser. A cartridge (not shown) is loaded in a barrel 52 into the slot 53 for the cartridge of the dispenser by a feeder. The dispenser includes a handle having a trigger 54 and trigger spring 58. The barrel further houses a piston 55. Activation of the trigger releases a spring 56 and causes the piston to move forward through the barrel 52 and contact the rear edge of the cartridge. Upon contact, the needle in the cartridge is forced to extend through a membrane of the cartridge and into the patient, injecting the patient with the liquid.

Figure 22:
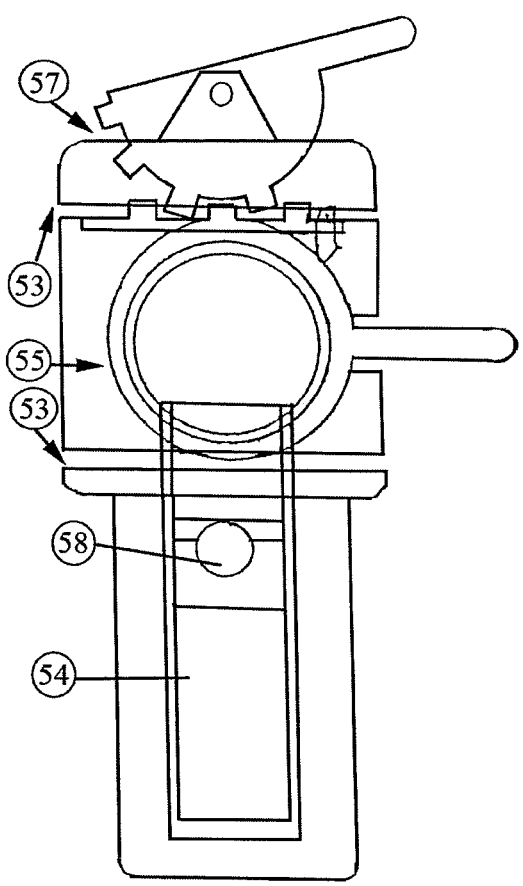
FIG. 22 is a front view of the continuous feed hypodermic syringe with self contained cartridge dispenser according to invention principles.

FIG. 22 is a front view of the continuous feed hypodermic syringe with self contained cartridge dispenser. A cartridge (not shown) is loaded in a barrel 52 of the dispenser by a feeder. The feeder includes a toothed gear which is part of a feeder gear assembly 57 that selectively engages a sprocket hole of the belt. The feeder pivots about a pivot point thereby causing the gear to rotate and move the belt along in either a clockwise or counterclockwise direction removing the spent cartridge from the barrel and replacing a new cartridge therein. As the feeder pivots to move the belt, once the cartridge is removed from the barrel, the gear will engage a section of the belt between the next two succeeding cartridges for moving the belt further along after the contents of the next adjacent cartridge are dispensed. A trigger 54, slot 53, a piston 55 and a trigger spring 58 are additionally shown and used as described above with respect to FIG. 21.

Figure 23:
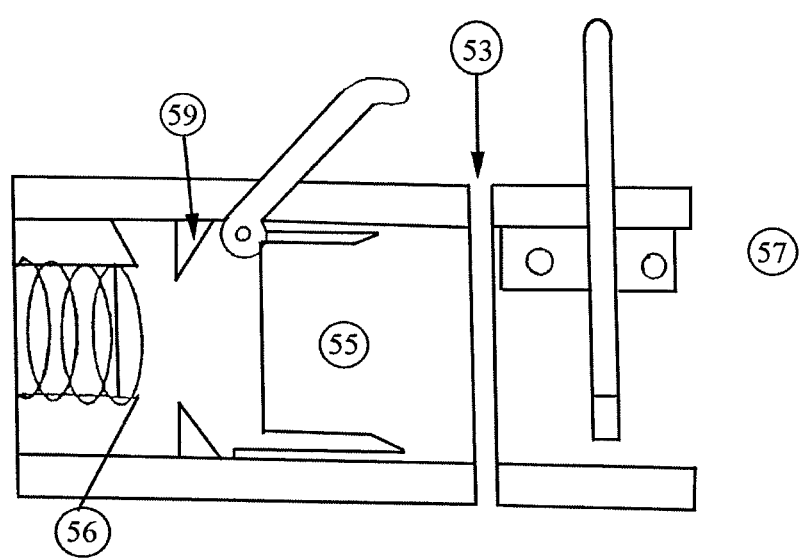
FIG. 23 is a top cross-sectional view of the continuous feed hypodermic syringe with self contained cartridge dispenser according to invention principles.

FIG. 23 is a top view of the continuous feed hypodermic syringe with self contained cartridge dispenser. A cartridge (not shown) is placed into the slot by the feeder gear assembly 57. The piston is held in position by a notched slot 59. When the piston has been activated, the piston is released from the notched slots and forced forward by a spring 56. The needle in the cartridge is then injected into the patient and the liquid dispensed.

Figure 24:
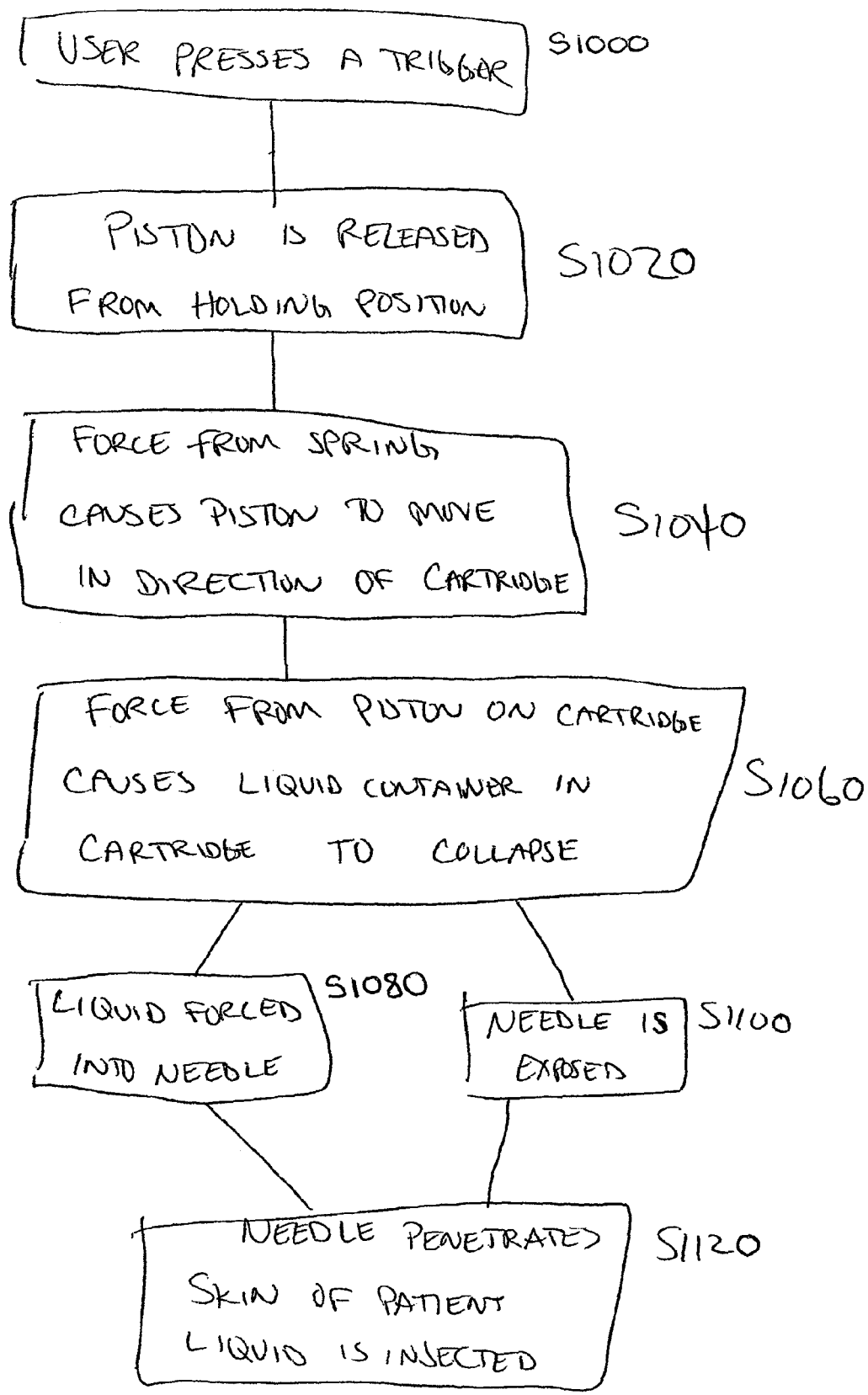
FIG. 24 is a flow diagram describing use of the continuous feed hypodermic syringe with self contained cartridge dispenser according to invention principles.

FIG. 24 is a flow diagram describing the dispensation of the vaccine using the continuous feed hypodermic syringe. The user depresses a trigger S1000 and releases a piston from a holding position S1020. The force from a spring causes the piston to travel along the length of the barrel in a direction towards a cartridge contained therein S1040. Upon contact with the cartridge the force exerted by the movable piston causes each of the vaccine containers and an accordion section of a cartridge core to collapse S1060. This simultaneously causes the needle to extend from the core S1100 and through a membrane and have the vaccine travel through the needle S1080. The needle penetrates the skin of the user and the user is vaccinated and receives the medication S1120.

Figure 25:
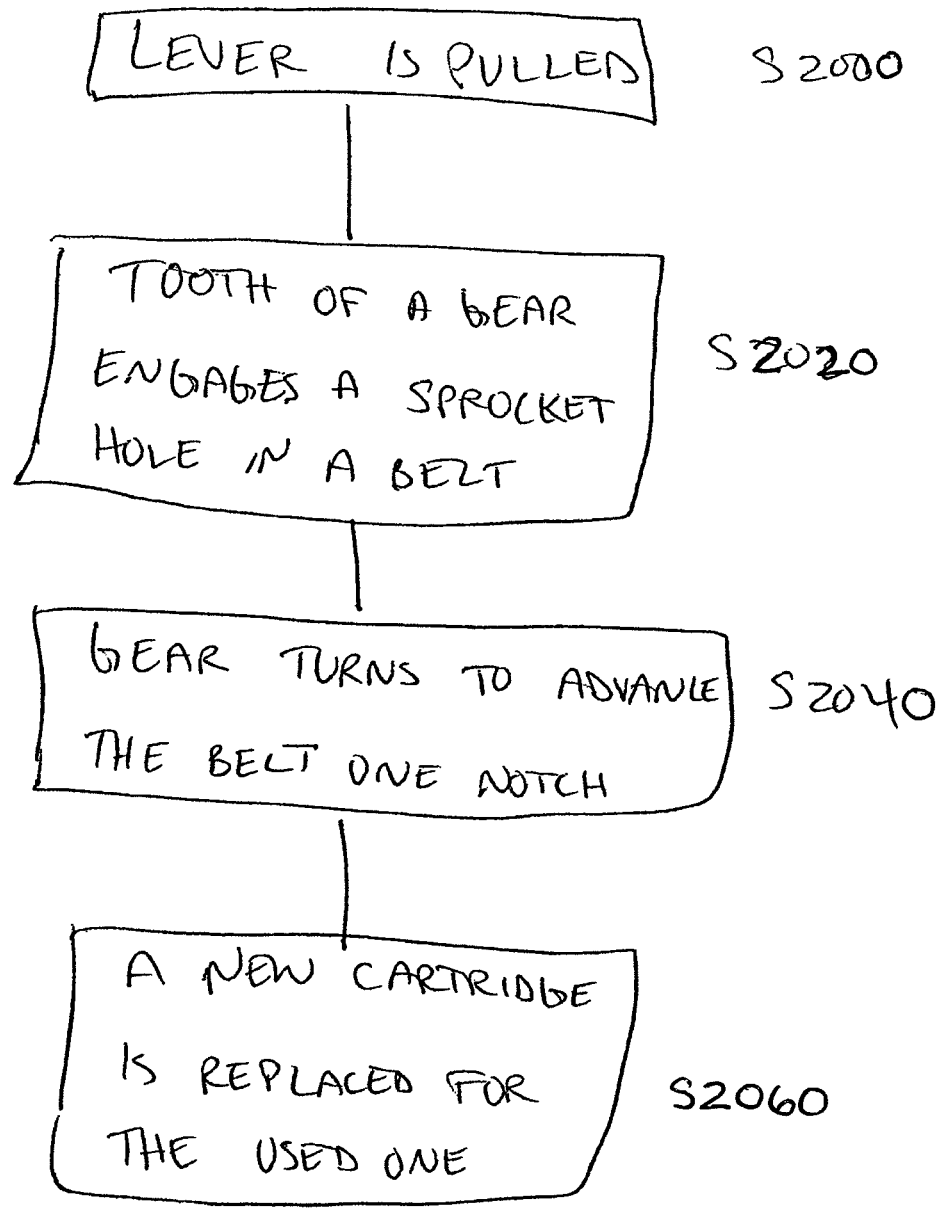
FIG. 25 is a flow diagram describing continuous loading of cartridges in the continuous feed hypodermic syringe with self contained cartridge dispenser according to invention principles.

FIG. 25 is a flow diagram describing the process of reloading of the continuous feed hypodermic syringe dispenser. A lever having a toothed gear extending into the barrel of the dispenser is moved S2000. A respective one of the gear teeth engages a sprocket hole in a clip/belt that contains the plurality of self contained cartridges S2020. The gear is rotated moving the belt one notch S2040 thereby removing the spent cartridge and replacing an unused cartridge within the barrel. The gear is caused to engage a subsequent sprocket hole in the belt. This process is repeated for dispending the contents of each subsequent cartridge S2060.

Figure 26:
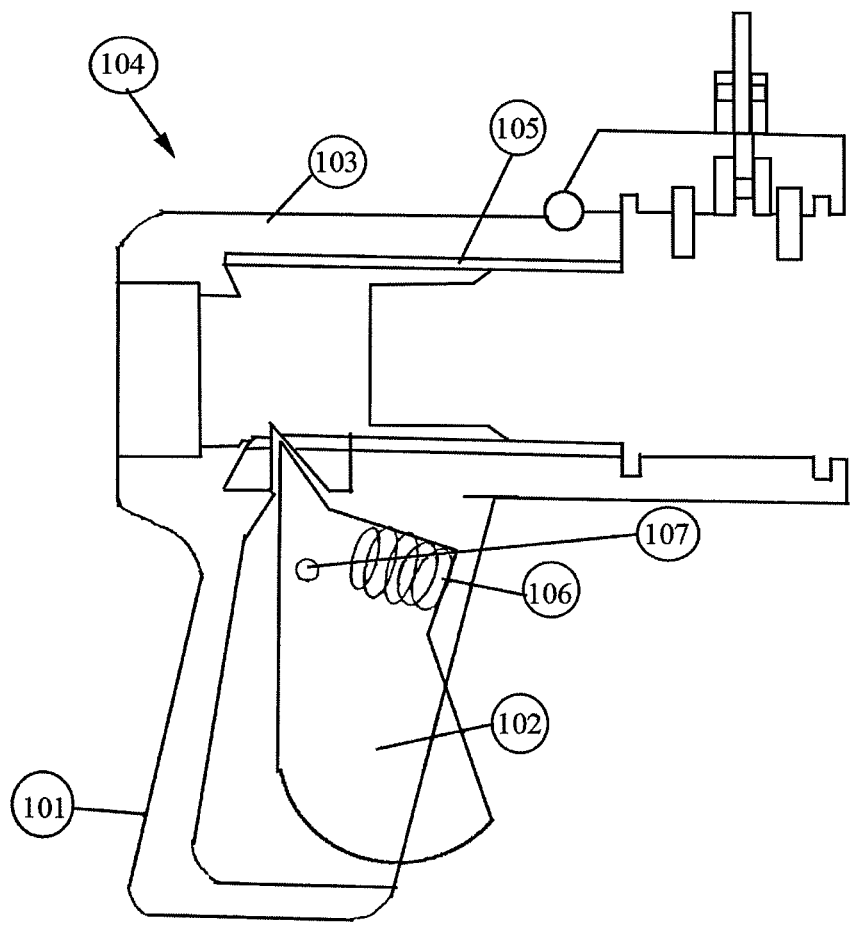
FIG. 26 is a side cross-sectional view of the continuous feed hypodermic syringe with self contained cartridge dispenser according to an additional embodiment of the invention principles.

FIG. 26 is a side view of the continuous feed hypodermic syringe with self contained cartridge dispenser 104, according to an additional embodiment. The cartridge (not shown), having a square shaped tube, is loaded in a barrel 103 of the dispenser 104 by a feeder. The dispenser 104 includes a handle 101 having a trigger 102 and a pivot point 107. The barrel 103 further houses a piston 105. Activation of the trigger 102 applies a force to the spring 106 causing the piston 105 to move forward through the barrel 103 and contact the rear edge of the cartridge. The rim on the cartridge withstands the impact and pressure from the spring driven piston. The raised lip further retains the cartridge tube in the dispenser and on the belt. The raised lip may also prevent the cartridge tube from being ejected from the dispenser when the piston pressure is applied to a rear edge of the cartridge. Upon contact, the needle in the cartridge extends through a membrane to inject the patient with the liquid.

Figure 27:
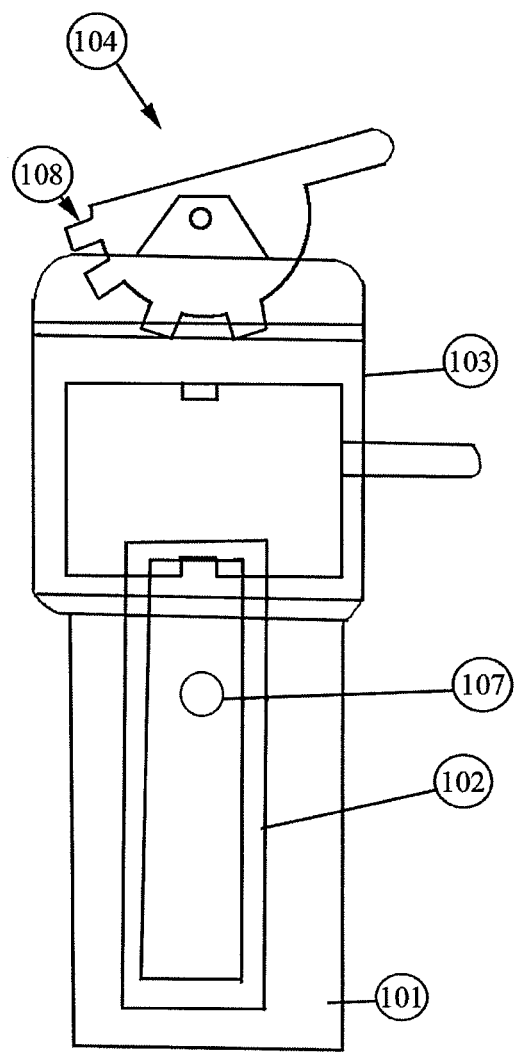
FIG. 27 is a front view of the continuous feed hypodermic syringe with self contained cartridge dispenser according to invention principles.

FIG. 27 is a front view of the continuous feed hypodermic syringe with self contained cartridge dispenser. The cartridge (not shown), having a square shaped tube in the present embodiment, is loaded in a barrel 103 of the dispenser 104 by a feeder. The feeder includes teeth that selectively engage sprocket holes 108 in the belt. The feeder pivots about a pivot point 107 thereby causing the gear to rotate and move the belt along in either a clockwise or counterclockwise direction removing the spent cartridge from the barrel and placing a new cartridge in the barrel. As the feeder pivots to move the belt, once the cartridge is removed from the barrel, the gear will engage a section of the belt between the next two succeeding cartridges for moving the belt further along and inserting an adjacent cartridge into the barrel. Handle 101 and trigger 102 are additionally shown in FIG. 27.

Figure 28:
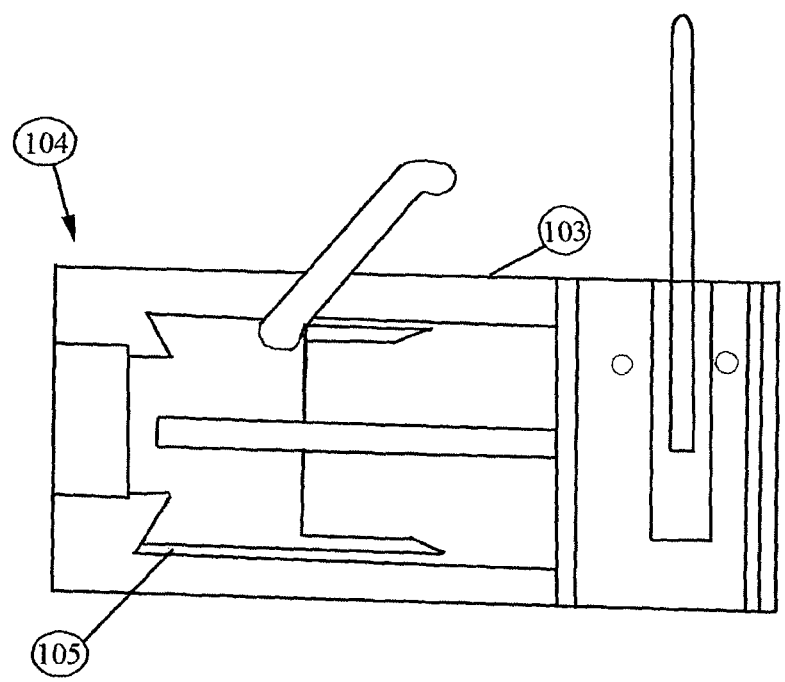
FIG. 28 is a top cross-sectional view of the continuous feed hypodermic syringe with self contained cartridge dispenser according to invention principles.

FIG. 28 is a top view of the continuous feed hypodermic syringe with self contained cartridge dispenser. The cartridge (not shown), having a square shaped tube in the present embodiment, is placed into the slot by the feeder gear assembly. The piston 105 is held in position by a notched slot. When the piston 105 has been activated, the piston 105 is released from the notched slots and forced forward by a spring. The needle in the cartridge is then injected into the patient and the liquid dispensed. Barrel 103 is additionally shown.

Figure 29:
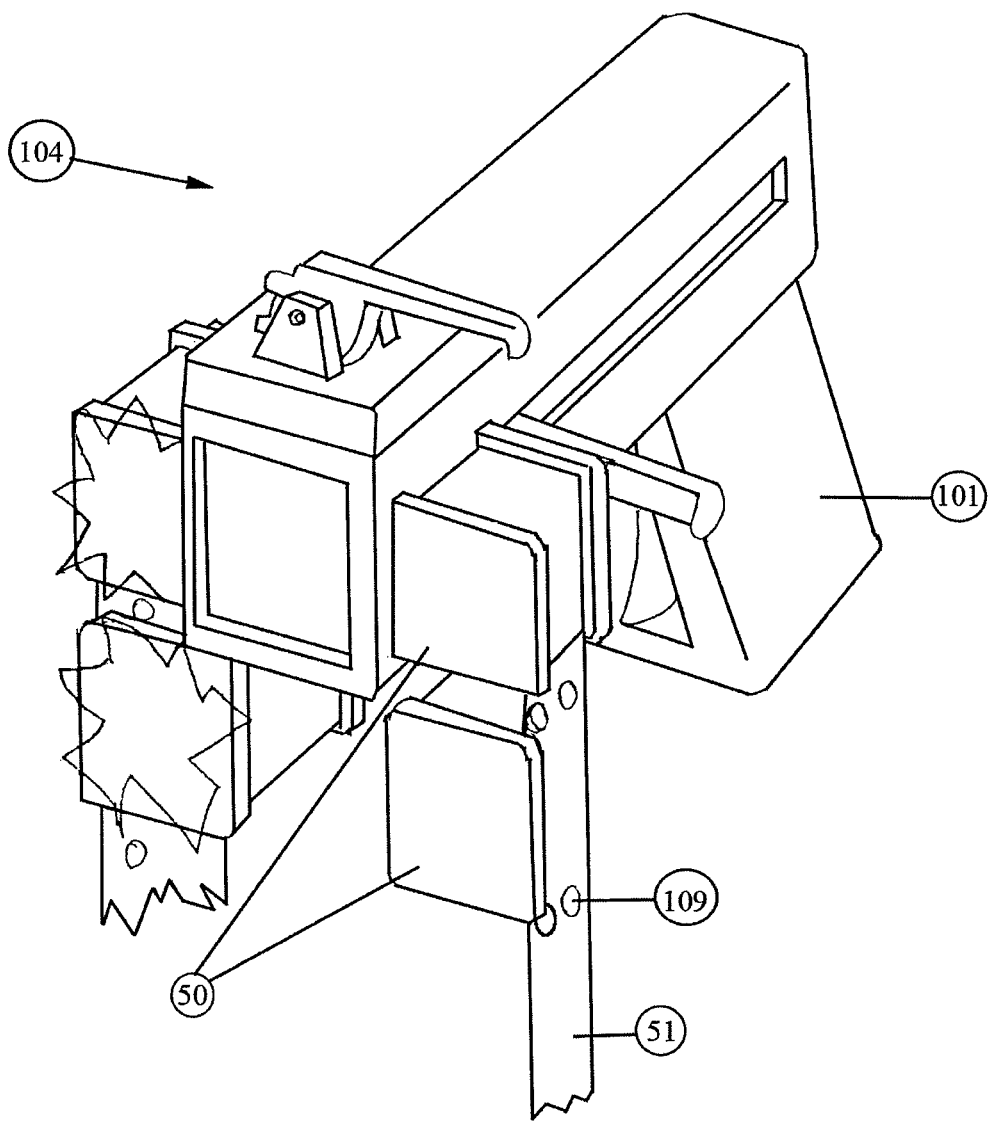
FIG. 29 is a perspective view of the continuous feed hypodermic syringe with self contained cartridge dispenser according to invention principles.

FIG. 29 is a perspective view of the continuous feed hypodermic syringe with self contained cartridge dispenser. A plurality of cartridges 50, having a square shape, is shown attached to a belt 51. Each cartridge 50 contains liquid to be dispensed to a patient. The cartridges are fed through the dispenser to quickly and efficiently dispense the liquids contained in the cartridges. The dispenser automatically and continuously dispenses a vaccine contained in one of a plurality of cartridges using a lever to actuate a piston that extends through a hollow barrel. An end of the piston contacts a rear edge of the cartridge and causes a needle to extend therefrom for insertion into a patient. Upon completion of the vaccination, a handle extending laterally outward from the barrel and connected to the piston is moveable to withdraw the piston from contact with the rear end of the cartridge thereby drawing the needle back into the cartridge. The movement of the handle causes a gear tooth within the barrel to rotate and engage a sprocket hole 109 extending through the belt 51. The rotation causes the belt to move in at least one of a clockwise or counterclockwise direction and remove the spent cartridge from the barrel and replace the spent cartridge with an unused cartridge for injection of a further patient.

While certain novel features have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is:

1. A cartridge for dispensing a liquid comprising:
    a housing having a channel extending therethrough and including a first membrane sealing a first end of the channel and a second membrane sealing a second end of the channel;
    a container positioned within the housing for retaining the liquid;
    a hollow needle positioned within the housing and forming an end cap sealing the container, the hollow needle extending from an end of the container and outside of said container towards said second membrane, said hollow needle receiving the liquid through an opening in the end cap;
    an accordion sleeve positioned within the housing and having a collapsible section and a tip section, said collapsible section extending from the end of the container and surrounding said hollow needle, said tip section extending from an end of said collapsible section opposite said container and comprising an edge sufficient to pierce said second membrane, said collapsible section is configured to be selectively collapsed, said tip section is configured to pierce said second membrane when said collapsible section is collapsed and said needle is caused to extend through said tip section and into a user, said liquid in said container being forced through said needle and into the user; and
    a disinfectant being positioned within a space formed between said housing, said accordion sleeve and said second membrane, wherein said tip section spreads the second membrane apart when it is pierced releasing disinfectant to sterilize an injection area and said needle passing through the second membrane.

2. The cartridge as recited in claim 1, wherein said hollow needle includes a base forming the end of said container opposite said first membrane, said base having a diameter greater than a diameter of said container.

3. The cartridge as recited in claim 1, wherein said liquid is a medicant.

* * * * *